United States Patent
Lamont et al.

(10) Patent No.: US 10,173,064 B2
(45) Date of Patent: *Jan. 8, 2019

(54) POWER SUPPLY DISCONNECT CURRENT MEASUREMENT FOR AN IMPLANTABLE MEDICAL DEVICE

(71) Applicant: Boston Scientific Neuromodulation Corporation, Valencia, CA (US)

(72) Inventors: Robert Graham Lamont, Van Nuys, CA (US); Damon Moazen, Northridge, CA (US); Robert D. Ozawa, Woodland Hills, CA (US); Thomas W. Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/647,006

(22) Filed: Jul. 11, 2017

(65) Prior Publication Data

US 2017/0304626 A1 Oct. 26, 2017

Related U.S. Application Data

(63) Continuation of application No. 15/177,038, filed on Jun. 8, 2016, now Pat. No. 9,713,718, which is a (Continued)

(51) Int. Cl.
*A61N 1/36* (2006.01)
*A61N 1/378* (2006.01)
(Continued)

(52) U.S. Cl.
CPC ....... *A61N 1/36125* (2013.01); *A61N 1/3706* (2013.01); *A61N 1/378* (2013.01); *A61N 1/37252* (2013.01); *A61N 1/3782* (2013.01)

(58) Field of Classification Search
CPC .............. A61N 1/36125; A61N 1/3706; A61N 1/37252; A61N 1/378; A61N 1/3782
See application file for complete search history.

(56) References Cited

U.S. PATENT DOCUMENTS

| | | |
|---|---|---|
| 4,686,990 A | 8/1987 | Moberg |
| 5,350,403 A | 9/1994 | Stroetmann et al. |

(Continued)

FOREIGN PATENT DOCUMENTS

| | | |
|---|---|---|
| EP | 0360551 | 3/1990 |
| WO | 2013/119439 | 8/2013 |

*Primary Examiner* — Paula J Stice
(74) *Attorney, Agent, or Firm* — Lewis & Reese, PLLC

(57) ABSTRACT

An implantable medical device (IMD) is disclosed having measurement circuitry for measuring one or more currents in the IMD, such as the currents drawn from various power supply voltages. Such currents are measured without disrupting normal IMD operation, and can be telemetered from the IMD for review. Switching circuitry in line with the current being measured is temporarily opened for a time period to disconnect the power supply voltage from the circuitry being powered. A voltage across a capacitance in parallel with the circuitry is measured when the switching circuitry is opened and again closed at the end of the time period, with the circuitry drawing power from the charged capacitance during this time period. The average current drawn by the power supply voltage is determined using the difference in the measured voltages, the known capacitance, and the time period between the measurements.

20 Claims, 16 Drawing Sheets

Related U.S. Application Data continuation of application No. 14/502,603, filed on Sep. 30, 2014, now Pat. No. 9,364,673.

(60) Provisional application No. 61/891,730, filed on Oct. 16, 2013.

(51) Int. Cl.
*A61N 1/372* (2006.01)
*A61N 1/37* (2006.01)

(56) References Cited

U.S. PATENT DOCUMENTS

| | | | |
|---|---|---|---|
| 5,391,193 | A | 2/1995 | Thompson |
| 5,713,939 | A | 2/1998 | Nedungadi et al. |
| 5,769,873 | A | 6/1998 | Zadeh |
| 5,994,876 | A | 11/1999 | Canny et al. |
| 6,898,463 | B2 | 5/2005 | Dropps et al. |
| 7,191,005 | B2 | 3/2007 | Stessman |
| 7,580,749 | B2 | 8/2009 | Lyden |
| 7,852,052 | B2 | 12/2010 | Vernon |
| 8,214,164 | B2 | 7/2012 | Gandhi et al. |
| 8,478,404 | B2 | 7/2013 | Maile et al. |
| 2009/0048643 | A1 | 2/2009 | Erickson |
| 2009/0273349 | A1 | 11/2009 | Rondoni |
| 2013/0073008 | A1* | 3/2013 | Ternes ............... A61N 1/36153 607/62 |
| 2014/0214113 | A1 | 7/2014 | Greiner |

* cited by examiner

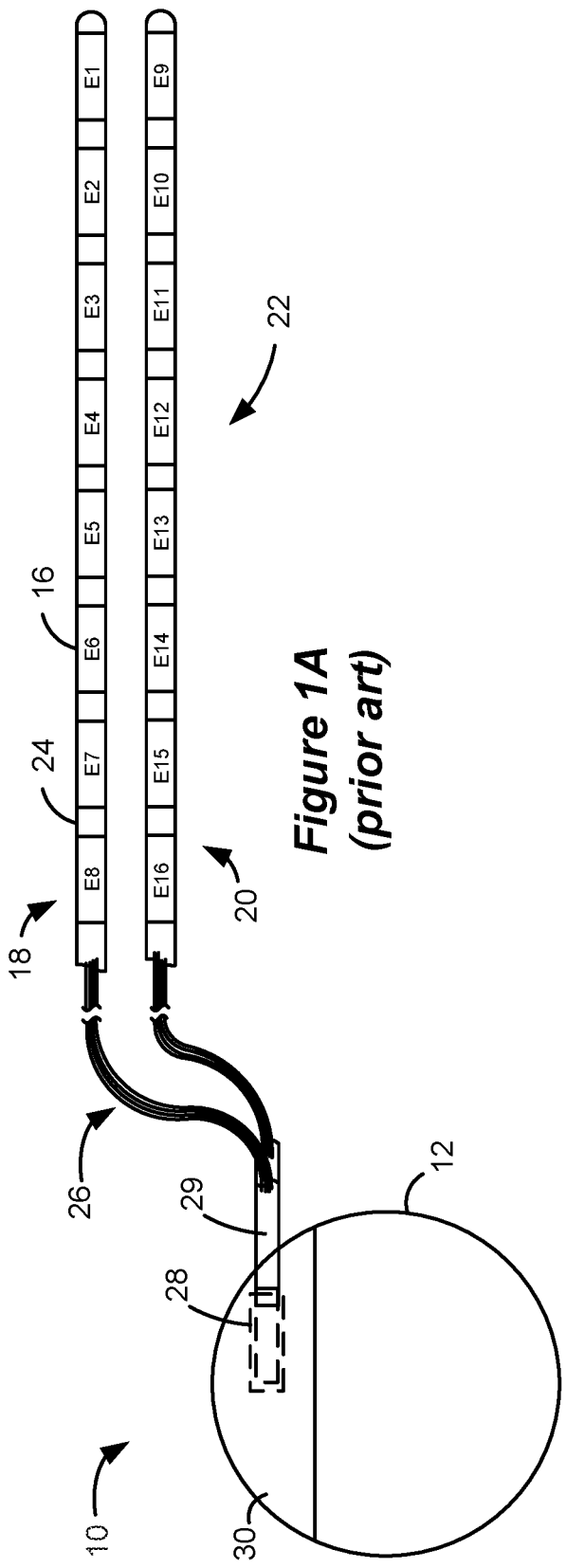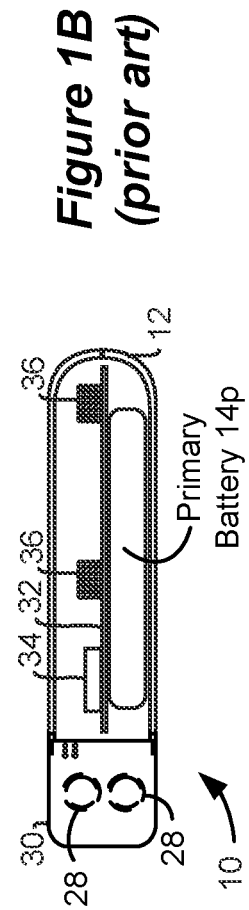
Figure 1A (prior art)
Figure 1B (prior art)

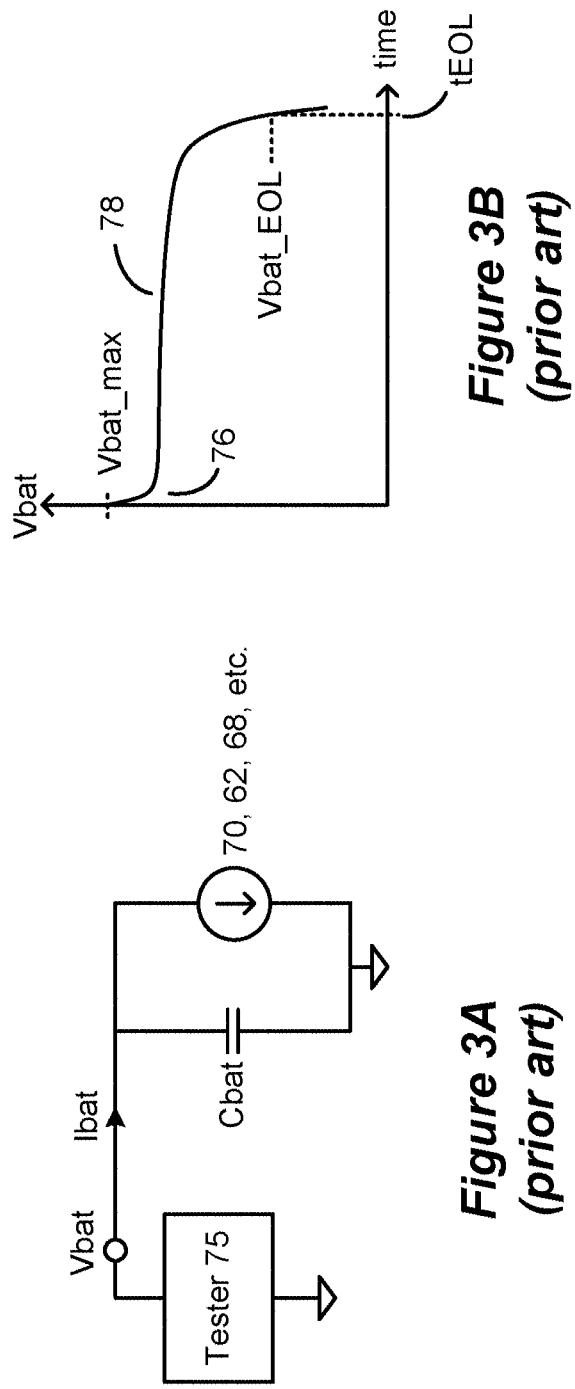

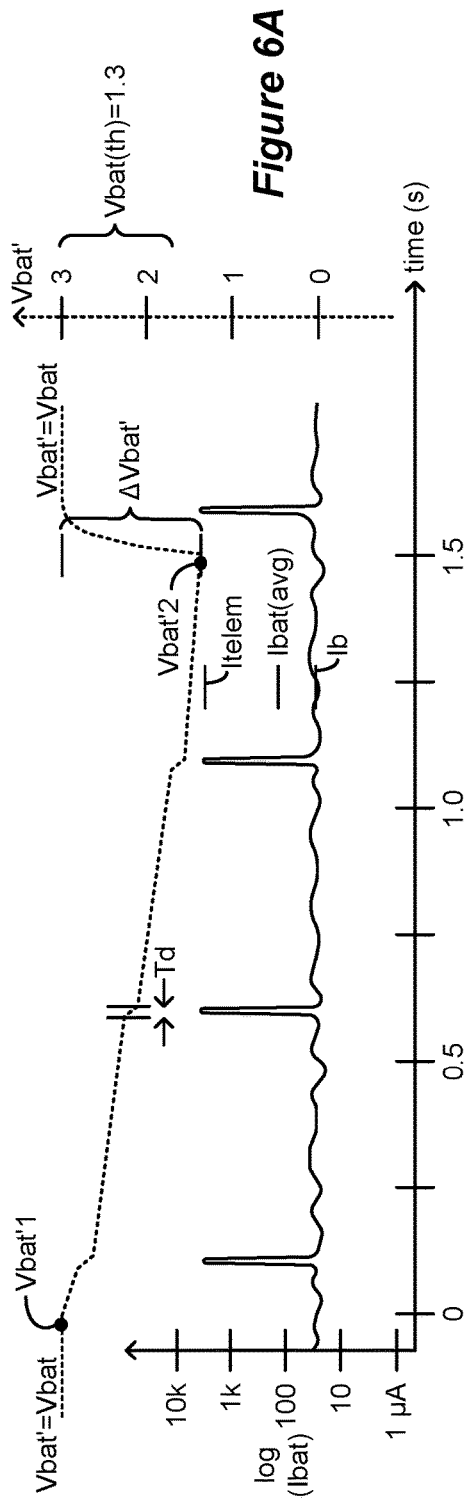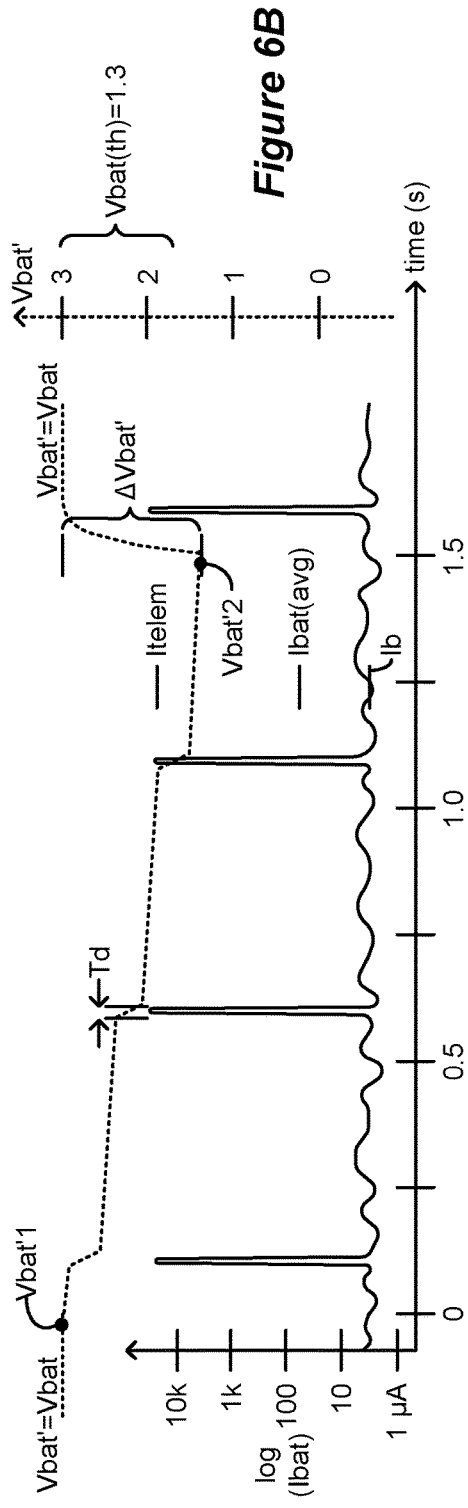

POWER SUPPLY DISCONNECT CURRENT MEASUREMENT FOR AN IMPLANTABLE MEDICAL DEVICE

CROSS REFERENCE TO RELATED APPLICATIONS

This is a continuation of U.S. patent application Ser. No. 15/177,038, filed Jun. 8, 2016 (now U.S. Pat. No. 9,713, 718), which is a continuation of U.S. patent application Ser. No. 14/502,603, filed Sep. 30, 2014 (U.S. Pat. No. 9,364, 673), which is a Non-Provisional of U.S. Provisional Patent Application Ser. No. 61/891,730, filed Oct. 16, 2013. Priority is claimed to these applications, and they are incorporated herein by reference in their entireties.

FIELD OF THE INVENTION

The present invention relates to implantable medical device systems, and in particular to systems involving implantable stimulators.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIG. 1A, an SCS system typically includes an Implantable Pulse Generator (IPG) 10, which includes a biocompatible device case 12 formed of a conductive material such as titanium for example. The case 12 typically holds the circuitry and battery 14 necessary for the IPG to function, as described in detail below. The IPG 10 is coupled to distal electrodes 16 designed to contact a patient's tissue. The distal electrodes 16 are coupled to the IPG 10 via one or more electrode leads (two such leads 18 and 20 are shown), such that the electrodes 16 form an electrode array 22. The electrodes 16 are carried on a flexible body 24, which also houses the individual signal wires 26 coupled to each electrode. In the illustrated embodiment, there are eight electrodes on each of leads 18 and 20, although the number of leads and electrodes is application specific and therefore can vary. The leads 18 and 20 contain proximal electrode contacts 29 that couple to the IPG 10 using lead connectors 28 fixed in a non-conductive header material 30 such as an epoxy.

As shown in the cross-section of FIG. 1B, an IPG 10 typically includes a printed circuit board (PCB) 32 to which various electronic components 34 are mounted, some of which are discussed below. A telemetry (antenna) coil 36 is used to transmit/receive data to/from an external device (not shown) through the patient's tissue. Such wireless communications can occur using different hardware and protocols, such as Frequency Shift Keying, Bluetooth, Bluetooth Low Energy, WiFi, Zigbee, etc. See, e.g., U.S. Patent Application Publication No. 2015/0073498.

IPG 10 in the depicted example contains a non-rechargeable primary battery 14p (where "p" denotes "primary"). Unlike a rechargeable battery, the electrochemical reaction in a primary battery 14p is not reversible by passing a charging current therethrough. Instead, a primary battery 14p will eventually expend the materials in one or both of its electrodes, and thus has a limited life span. Once the battery 14p is exhausted, it will be necessary to explant IPG 10 from the patient so that the battery 14p can be replaced and the IPG 10 re-implanted, or (more likely) so that a new IPG 10 with a fresh battery 14p can be implanted. Primary batteries 14p can be formed using different chemistries, but Lithium CFx batteries or Lithium/CFx-SVO (Silver Vanadium Oxide) hybrid batteries are popular for use in implantable medical devices, and produce battery voltages, Vbat, between 1.2 and 3.2 Volts in one example. As described further with respect to FIG. 3B below, Vbat will decrease over time as the primary battery 14p is used over the life of the IPG 10.

FIG. 2 shows an architecture 5 for IPG 10, which is described in U.S. Patent Application Publication 2013/0331910, and which is incorporated herein by reference. Shown with particular emphasis are the various power supplies in the IPG 10, which are shown with thicker lines. Only a few other non-power supply signals are shown in FIG. 2 to the extent they are discussed below, and such signals are shown with thinner lines. One skilled in the art will appreciate that the IPG 10 contains many such "regular" signal lines, and may contain other power supplies, which are not shown for convenience.

Primary battery 14p provides the main power supply voltage, Vbat, from which all other power supply voltages in the IPG 10 are derived. Some circuits, such as a DC-DC converter 62 and tank circuitry 68, described further below, receive power directly from Vbat. Other power supplies voltages needed in IPG 10 may be higher than Vbat, and so are generated using a boost converter 70, which produces a higher power supply voltage, Vup, from Vbat. Vup may be 3.2 V in one example. Boost converter 70 can comprise a capacitor-based change pump, an inductor-based step-up converter, or a combination of these. See, e.g., U.S. Pat. No. 7,872,884.

As shown, architecture 5 contains analog circuitry 52, digital circuitry 54, and memory 60, each of which are powered by their own power supply voltages Vd, Va, and Vf, each of which is generated from Vup via regulators 44, 46, and 48. Regulators 44, 46, and 48 can comprise low drop out linear regulators that use little power and that create less noise than switching regulators. Even if the power supply voltages Vd, Va, and Vf are of the same magnitude (e.g., 2.8 V) in the IPG 10, it is useful to isolate them via the regulators to prevent noise on one power supply from affecting the other. For example, digital circuitry 54 may create noise on Vd as it switches, which noise could potentially affect Va and hence performance of analog circuitry 52 if not isolated. Memory 60 (e.g., a Flash EPROM) preferably has its own regulator 48 because it may consume a large amount of current (e.g., when being programmed or erased), which Vf and regulator 48 must supply. Additionally, regulator 48 can be disabled from time to time to save power.

Analog circuitry 52 powered by Va includes a number of circuits, including thermistors for measuring temperature (T), band gap generators for producing temperature-insensitive reference voltages (Vref), oscillators and clock generation circuitry (CLK), telemetry circuitry 72 including modulation and demodulation circuitry, analog measurement circuitry 74, and the like.

Digital circuitry 54 comprises the digital circuits in the IPG 10 that are powered by power supply voltage Vd, and include a microcontroller 58 and various timing circuits 56. Digital circuitry 54 can be integrated, at least in part, on a single mixed-mode Application Specific Integrated Circuit (ASIC) with at least some of the analog circuitry 52, as shown for example in U.S. Patent Application Publications 2008/0319497 and 2012/0095529. Digital circuitry 52 can also be discrete from the analog circuitry 54. For example, the ASIC of the '497 and '529 Publications can used in conjunction with Texas Instruments microcontroller 58 part number MSP 430 for example, which is described in data sheets stored on Texas Instruments' website, which data sheets are incorporated herein by reference. Microcontroller 58 may also comprise a microprocessor integrated circuit, a collection of integrated circuits, a collection of non-integrated circuits, or a collection of both integrated and non-integrated circuits—essentially any hardware capable of operating the IPG 10 in the manners disclosed herein.

Memory 60, powered by power supply voltage Vf, can hold the operating software for the IPG 10 (e.g., for the microcontroller 58), and can also act as a free space to store data, such as logged data to be wirelessly telemetered to an external device for analysis and/or to provide feedback to the patient, clinician, or IPG manufacturer. Memory 60 can also store data transmitted from an external device, such as the therapy settings for a given patient, such as which electrodes 16 are active to provide current pulses, and the magnitude, polarity, frequency, and, width of those pulses. Such therapy settings are sent from the microcontroller 58 to one or more Digital-to-Analog Converters (DAC(s)) 64, which generate the specified current pulses accordingly (Iout). See, e.g., U.S. Patent Application Publication 2007/0100399. Only one electrode 16 is shown in FIG. 2 for simplicity, but one skilled on the art will understand that therapy settings would involve more than one electrode. For example, another electrode 16 (which could include the conductive case 12; FIG. 1A) would be used to provide a return path for Iout to prevent the build-up of charge in the patient's tissue. Additionally, more than one electrode 16 may be used to source current to the patient's tissue, and more than one electrode 16 may be used to sink current from the patient's tissue. See, e.g., U.S. Patent Application Publications 2013/0184794 and 2013/0006315.

The power (e.g., magnitude) of the current pulses at the electrodes 16 can differ from time to time for a given patient, or from patient to patient. Accordingly, the power supply voltage for the DAC(s) 64, called the compliance voltage (V+), is not fixed, but is instead set at an optimal level via a feedback loop. V+ monitor and adjust circuit 66 monitors a voltage in line with the active electrode(s) 16, which it uses to control the DC-DC converter 62 to generate a power supply voltage V+ of an appropriate magnitude for the DAC(s) 64. See, e.g., U.S. Pat. No. 7,444,181, U.S. Patent Application Publications 2010/0211132, 2013/0289665, and 2013/0310897. Such adjustment of V+ is desired because if V+ is too low, DAC(s) 64 will become "loaded" and unable to provide the specified current, Tout. If V+ is too high, DAC(s) 64 will be able to provide the desired current, but power will be wasted, with some portion of the compliance voltage V+ being dropped across the DAC(s) 64 without any useful effect. See, e.g., U.S. Pat. Nos. 7,539,538 and 7,872,884. As noted earlier, DC-DC converter 62 produces V+ directly from Vbat, and the converter 62 (like boost converter 70) can comprise a capacitor-based change pump, an inductor-based step-up converter, or combination of these. V+ may be set by the converter 62 in one example between 3 to 18 Volts, again depending on power of the current the DAC(s) 64 must provide.

Tank circuitry 68 is coupled to the telemetry coil 36, and like DC-DC converter 62 is directly powered by Vbat. Tank circuitry 68 can comprise a tuning capacitor (not shown) which operates in conjunction with the inductance of the coil 36 to set the tank's resonant frequency as necessary for communications with an external device. Tank circuitry 68 also includes transistor switches controlled by modulation circuitry within telemetry circuitry 72, which modulation circuitry converts digital data from the microcontroller 58 to be transmitted to signals that switch the transistor switches at or near the resonant frequency. When receiving data, the tank circuitry 68 is coupled to demodulation circuitry within telemetry circuitry 72 for extracting the digital data from the received signal for interpretation by the microcontroller 58. See, e.g., U.S. Patent Application Publication U.S. 2009/0069869 and U.S. Pat. No. 8,081,925.

An issue of concern to IPG manufacturers is IPG quality and reliability, and in this regard manufacturers often employ testing to ensure that IPGs are not defective. For example, prior to insertion of the IPG's circuitry within its case 12, when the circuitry is still accessible and before the battery 14p is connected to it, manufacturers often run various tests to see whether the IPG is drawing too much current. This could occur for example if a defect in the IPG circuitry is causing current leakage from a power supply voltage (or other voltages) to ground. If such current leakage is present, the IPG 10 may simply not work, or the primary battery 14p, once connected, may deplete more quickly than it should. Faster-than-normal battery depletion is particularly concerning for primary-battery IPGs, because as noted earlier, the IPG must be explanted when the battery is expended, with substantial inconvenience to the patient.

An example of IPG testing at this stage is shown in FIG. 3A. A tester 75 is coupled to the Vbat node in the IPG circuitry (i.e., the node to which the positive terminal of the battery 14p will ultimately be connected). The tester 75 biases this node to a proper voltage to power the IPG 10 (e.g., Vbat=3.0V), and measures the current draw through that node, Ibat, which comprises the total current drawn by the IPG 10. Although not shown, tester 75 would also likely couple to other nodes such as a connector in the IPG circuitry to provide the signaling necessary to operate the IPG 10 normally, thus allowing Ibat to be determined under realistic use conditions. If Ibat as determined by the tester 75 is unusually high (e.g., above a threshold Ibat'), the IPG 10 under test may be deemed faulty, and thus not further manufactured or shipped. One skilled in the art will recognize that other tests of the IPG 10 can be run at this stage beyond determination of Ibat.

However, testing currents is difficult to accomplish once the IPG circuitry has been connected to its battery 14p, sealed inside its case 12, and is no longer accessible. Nonetheless, the inventors consider it desirable to determine such currents at this stage, because manufacturing steps associated with encasing the IPG circuitry and connecting additional structures (such the battery 14p) can give rise to additional defects that are desirable to discover.

A method employed by IPG manufacturers to infer IPG current draw at this stage, at least for IPGs having wirelessly-rechargeable batteries 14r (where "r" denotes "rechargeable") (see FIGS. 11A-11C), is to: charge the battery 14r; wirelessly transmit its voltage (Vbat1) to an external device; operate the IPG 10 normally for some period of time (e.g., a one week "burn-in"); wirelessly transmit its voltage thereafter (Vbat2); and then determine the difference in the battery voltage before and after (ΔVbat=Vbat1−Vbat2). The resulting ΔVbat can then be compared to a threshold (Vbat(th)), and if ΔVbat>ΔVbat (th), the manufacturer can conclude that the IPG 10 is drawing too much current from the battery 14r, and that the IPG 10 is not acceptable at least from this perspective.

This approach however is problematic when applied to the testing of a primary-battery IPG for a number of reasons. First, and as shown in FIG. 3B, the discharge curve of a primary battery (Vbat as a function of time, assuming a constant current draw) is non-linear. It comprises a drop-off portion 76 where Vbat falls relatively quickly early in its use, and later enters a relatively flat portion 78 where Vbat falls slowly, at least until the End Of Life (EOL) of the battery is reached (i.e., at voltage Vbat_EOL, at which point the battery 14p can no longer operate the IPG's circuitry). Experience teaches that primary batteries 14p when purchased new are not consistent in where they seem to be currently operating on this discharge curve. Some new batteries seem to be at the beginning of their drop-off portion 76, and thus fall quickly upon use, while others seem to have surpassed the drop-off portion 76 to at least some degree, and are thus closer to, or in, the flat portion 78. Thus, for the same burn-in time, different values for ΔVbat could result, even if the primary-battery IPGs being tested in fact are drawing the same amount of current, Ibat. In other words, ΔVbat is not a good predictor of current draw for a primary battery 14p.

Second, Vbat for a primary battery 14p will fall slowly compared to a rechargeable battery 14r, even if the primary battery 14p is still within its drop-off portion 76. As a result, a meaningful burn-in time for primary-battery IPGs would need to be substantially longer than a week to see significant differences in ΔVbat, such as months, which is impractical for the manufacturer. Moreover, the months of burn-in permanently deplete the primary battery 14p to some degree, which amounts to shortening the useful life of the IPG 10 by an equivalent amount. (Note that this is not a concern for a rechargeable-battery IPG 10, because after a relatively-short burn-in period, an acceptable IPG 10 exhibiting a suitably small ΔVbat can have its battery 14r recharged before the IPG 10 is shipped).

The inventors have conceived of ways to measure current draws after primary-battery IPG 10 manufacturing is complete, and one way is shown in FIG. 3C (which may be inventive and is not admitted as prior art). In this example, current measurement circuitry 55 includes a measurement resistor Rm placed in line with Ibat between the battery 14p and the remainder of the IPG circuitry. Rm would preferably be small (e.g., 1 ohm) so as not to waste battery power (e.g., Ibat$^2$*Rm), and may comprise an already-existing component in the path, such as a fuse. As Ibat passes through Rm, a voltage Vm (Ibat*Rm) builds up across Rm, which can be measured with a differential amplifier 73. This measurement voltage Vm can be digitized at an Analog-to-Digital (A/D) converter 74, which comprises part of measurement circuitry 74 (FIG. 2), and which is usually present in an IPG 10 and used for other reasons. Thereafter, microcontroller 58 can wirelessly transmit Vm (or Ibat, by dividing Vm by the known value of Rm) to an external device using telemetry circuitry 72 for the manufacturer's review.

As such, a manufacturer can use the current measurement circuitry 55 of FIG. 3C to assess Ibat even after IPG manufacture is complete, and thus can determine whether Ibat is high enough to suggest a defect and thus that the IPG should not be shipped. Advantageously, this measurement occurs without the need of a burn-in period of long duration that would at least partially deplete the primary battery 14p.

However, while the current measurement circuitry 55 of FIG. 3C is certainly plausible, it is not necessarily realistic to implement in all IPG designs. This is in part due to the varying nature of Ibat during normal operation of the IPG 10. As shown in FIG. 3D, Ibat is not generally constant, but contains high-current draw spikes (Itelem). Indeed, as the logarithmic y-axis scale in FIG. 3D makes clear, these current spikes can be 1000 times larger than the baseline current (Ib) between them.

These current spikes result from the communication scheme used between the IPG 10 and an external device, which is discussed in U.S. Pat. Nos. 7,725,194 and 8,131,377, which are briefly explained. While the IPG 10 is designed to wirelessly communicate with an external device, it is not practical to constantly provide power to the IPG's telemetry circuitry 72 to allow the IPG 10 to determine when an external device is attempting to communicating with it. Receiver circuitry within the IPG's telemetry circuitry 72 draws too much power to permit this. Instead, the IPG 10 powers its receiver circuitry only during listening windows of a small duration (e.g., Td=20 msec), which issue periodically (e.g., Tp=0.5 s). It is incumbent on the external device wishing to communicate with the IPG 10 to continuously broadcast a wake-up signal for a duration of at least Tp, and preferably longer, to ensure that the IPG 10 can sense such wake-up signal during at least one of its listening windows. If the IPG 10 so senses the wake-up signal, it can then power its receiver circuitry (and possibly also its transmission circuitry if the IPG 10 needs to transmit data) for as long as necessary to communicate with the external device during a communication session, after which it can revert to periodically issuing listening windows once again.

Thus, Ibat in FIG. 3D is high during these listening window periods (Td) as the telemetry circuitry 72 draws current Itelem from power supply voltage Va. By comparison, the base line current Ib drawn between these windows is relatively small, when the IPG is otherwise drawing current from various analog 52, digital 54, and memory 60 circuitry during its normal operation, such as providing patient therapy.

While current measurement circuitry 55 of FIG. 3C theoretically allows Ibat to be determined, Ibat is not so easily determined in the IPG 10 as a practical matter. First, the differential amplifier 73 must have a large dynamic range able to accurately resolve small voltages over the orders of magnitude by which Ibat varies. For example, for typical Ibat currents (from Ib to Itelem), and assuming a measuring resistor of Rm=1 ohm, Vm will range from a few microVolts to a few milliVolts, which voltages are difficult to measure.

Second, the A/D 74 may not be well suited to meaningfully interpret Ibat via Vm. Although an A/D 74 is typically present in an IPG 10 to measure various voltages during IPG operation, A/D 74 may not be configured to sample measured voltages at a rate necessary to resolve Ibat. In this regard, Ibat can have current variations of even shorter durations that the listening windows, for example, as small as microseconds in duration. If one assumes that A/D 74 must capture current variations in Ibat as small as one microsecond, it must sample Ibat at least every 0.5 microseconds (per well-known sampling rules). This would amount to two million samples per second—a large amount of data that the IPG 10 may not be able to store. This problem is exacerbated by the need to sample Ibat for long enough to pick up at least a few of the current spikes, and thus Ibat may need to be sampled for longer than one second.

High sampling rates would also tax the A/D 74, which typically doesn't need to sample data at this rate during normal use in the IPG 10, and which may therefore be unable to do so. Even if A/D 74 can be configured to sample Ibat at an acceptable rate for test purposes, A/D 74, by virtue of its faster operation, could start to draw significant current, as could other circuitry in the IPG 10 attempting to handle the large amounts of data A/D 74 is providing. Such atypical use of the IPG 10 during this measurement would therefore increase Ibat, and would thus skew its measurement, as Ibat would not be reflective of normal IPG operation.

Finally, while the current measurement circuitry 55 of FIG. 3C is capable of measuring Ibat being drawn from power supply voltage Vbat, the inventors consider it desirable to determine the current draws from other power supply voltages in the IPG 10. This would be beneficial, as it would allow the manufacturer to understand which circuits in the IPG might be drawing excessive currents. For example, if the current being drawn from power supply voltage Vup is unusually high, it may suggest a problem in the regulators 44, 46, or 48 that draw current from this power supply voltage. Such excessive currents would ultimately contribute to Ibat, and thus may be noticeable in its measurement, but Ibat would be unable to reveal the source of the current leakage. Additionally, current leakage from a particular power supply voltage may be relatively small and thus not resolvable in Ibat, even if such leakage is still significant to the circuitry powered by that power supply voltage, which circuitry may be at least at risk of failure. Thus, the inventors recognize that the current measurement circuitry 55 of FIG. 3C could be included in line with all of the power supply voltage to determine their current draws, but again, a more practical current-measuring solution is desired.

BRIEF DESCRIPTION OF THE DRAWINGS

FIGS. 1A and 1B show an Implantable Pulse Generator (IPG) having a primary battery, and the manner in which electrodes are affixed to the IPG, in accordance with the prior art.

FIG. 3A shows testing the current drawn by IPG circuitry while accessible to a manufacturer and before connection of the IPG's battery, in accordance with the prior art.

FIG. 3B shows the discharge curve for the primary battery in accordance with the prior art.

FIGS. 6A-6C show examples in which the current measurement circuitry determines that the current drawn from the battery power supply voltage is excessive, in accordance with an embodiment of the invention.

DETAILED DESCRIPTION

Figure 2:
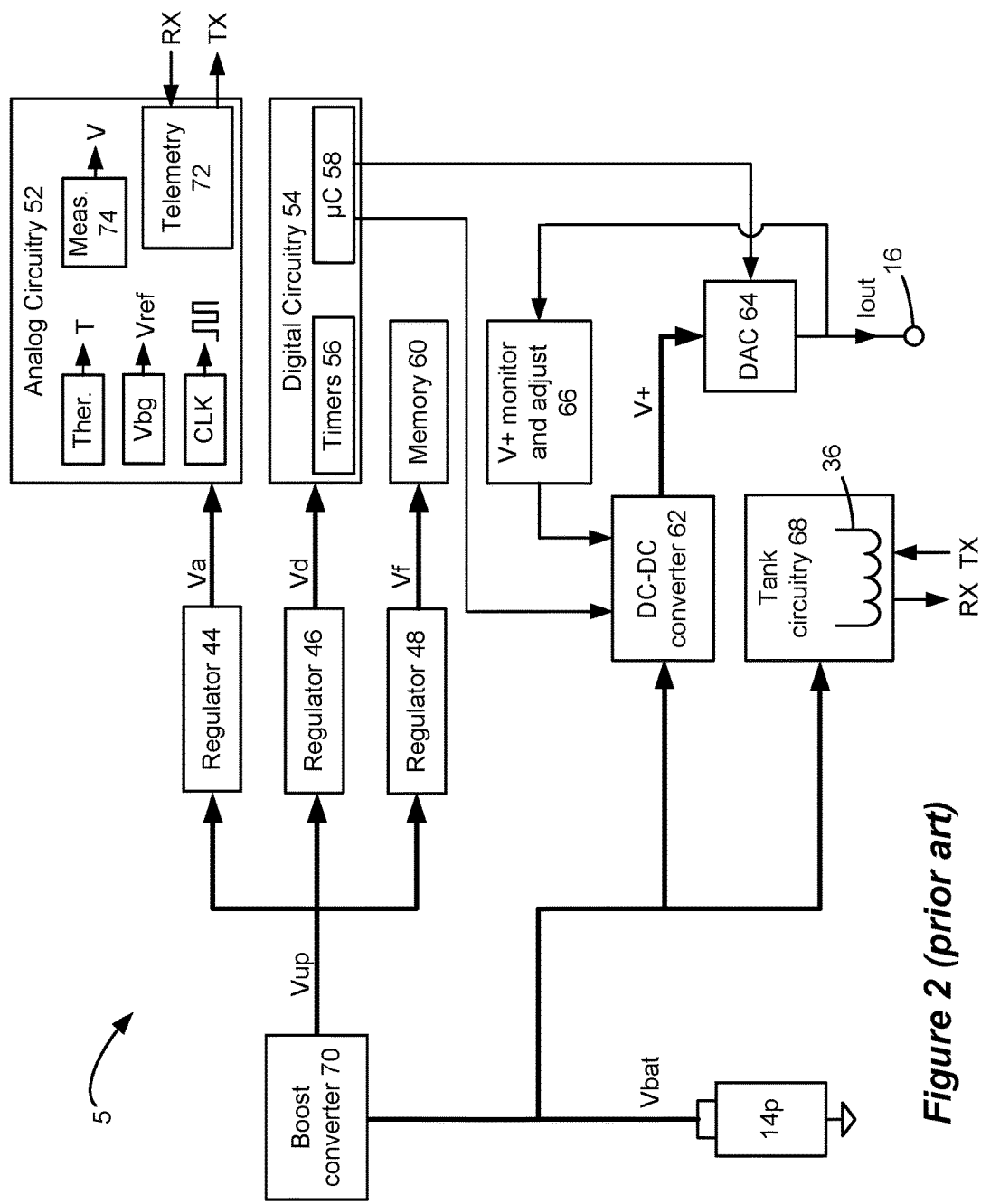
FIG. 2 shows the architecture of the IPG, including various power supply voltages, in accordance with the prior art.

An implantable medical device (IMD) such as an Implantable Pulse Generator (IPG) is disclosed having current measurement circuitry for measuring one or more currents in the IPG, such as the currents drawn from various power supply voltages, including the battery. The current measurement circuitry allows such currents to be measured while the IPG is operating normally using components typically present in the IPG, with such current measurements occurring in manners that don't overtax such components or skew the currents being measured. Moreover, such current measurements can be made after IPG manufacture when the IPG's circuitry is no longer accessible, and telemetered from the IPG to an external device for review.

The current measurement circuitry includes switching circuitry in line with the current being measured, which switching circuitry may already be present in the IPG at least in part, and used for purposes other than current measurement. When desired to measure a current, the switching circuitry is temporarily opened for a time period to disconnect the power supply voltage from the circuitry being powered by and drawing current from that power supply voltage. Such disconnection may also comprise disabling the circuitry that generates the power supply voltage. A capacitance in parallel with the circuitry, which may be intentionally added and is of known value, is charged by the power supply voltage when the switching circuitry is closed, and the voltage across this capacitance is measured preferably prior to opening the switching circuitry. After the switching circuitry is opened, the circuitry draws power from the charged capacitance and thus operates normally. The voltage on the capacitance will fall in accordance with its value and the amount of current being drawn by the circuitry. Before this voltage falls to a point that it can no longer continue powering the circuitry, the voltage across the capacitor is measured again, and the switching circuitry is closed at the end of the time period to reconnect the circuitry to the power supply, which circuitry continues to operate normally.

The average current drawn by the power supply voltage can then be determined using the difference in the measured voltages, the known capacitance, and the time period between the measurements. More specifically, the average current comprises the capacitance times the rate at which the measure voltage falls, which can be determined by dividing the difference in the measured voltages by the time period between the measurements while the switching circuitry is opened. If this measured current is merely represented by the difference in the measured voltages, this difference can be compared to a difference threshold to determine whether the current is too high, and perhaps suggestive of a defect in the IPG.

An improved architecture 100 for an IPG such as IPG 10 discussed earlier is shown in FIG. 4, and comprises switching circuitry 102 between the primary battery 14p, and the remainder of the IPG's circuitry. Otherwise, the circuitry in the IPG 10 is unchanged from that described earlier, and is thus not reiterated here.

Figure 5A:
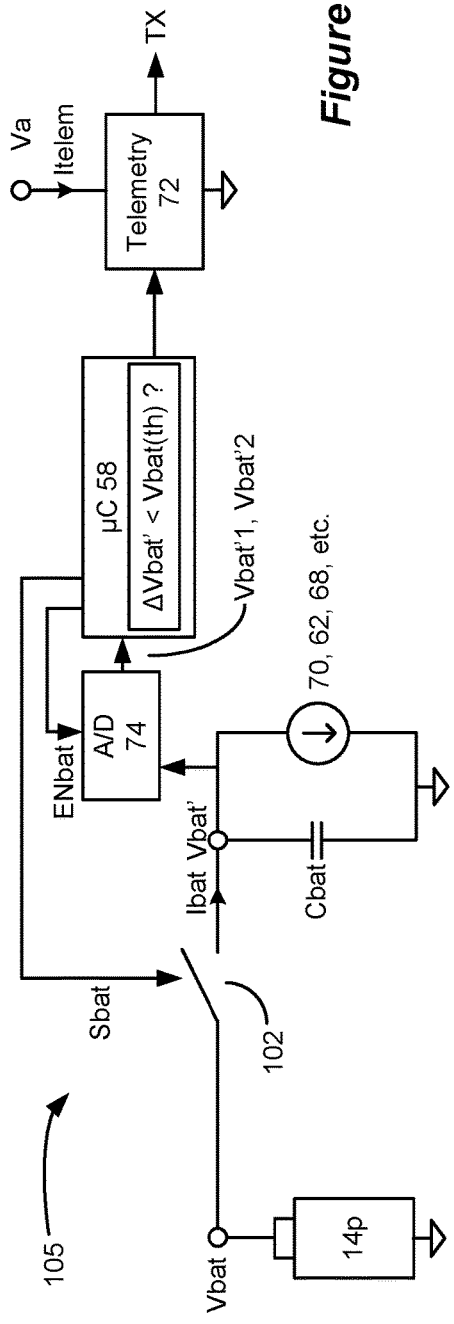
FIGS. 5A and 5B show operation of the current measurement circuitry in accordance with an embodiment of the invention, including measuring voltages when the switching circuitry is opened and closed, which voltage difference corresponds to the current drawn, in accordance with an embodiment of the invention.

Switching circuitry 102 is controlled by current measurement circuitry 105, shown in FIG. 5A, to determine the current being drawn from the battery 14p, Ibat, by temporarily disconnecting the battery 14p from the IPG circuitry. The components used in current measurement circuitry 105 are included in both the analog 52 and digital 54 circuitries, and are typically already present in the IPG and used for other purposes.

Note that the IPG circuitry is modeled in FIG. 5A as a variable current load, Ibat, in parallel with a capacitance, Cbat, and powered by a voltage, Vbat'. Vbat' comprises Vbat as supplied by the battery 14p when the switching circuitry 102 is closed, but is disconnected from Vbat when the switching circuitry 102 is opened. Cbat comprises, at least in part, inherent capacitances such as the input capacitances of the boost converter 70, the DC-DC converter 62, and the tank circuitry 68 to which the Vbat node is connected. However, in reality, the majority of the contribution to Cbat comes from one or more decoupling capacitors intentionally added across the IPG circuitry. As one skilled in the art will realize, the addition of such decoupling capacitor(s) acts to filter and stabilize Vbat. Cbat in FIG. 5A may be 56 µF in one example.

This capacitance Cbat is used to measure Ibat without disrupting normal operation of the IPG circuitry. This occurs as follows: switching circuitry 102 is first closed using control signal Sbat=0 issued from the microcontroller 58, Vbat and Vbat' are connected and Cbat is charged accordingly, and the IPG 10 is operated normally. Switching circuitry 102 is then opened for a short time period (Tbat) (Sbat=1), thus disconnecting the battery 14p from the IPG circuitry, i.e., disconnecting Vbat' from Vbat. Vbat' is measured (Vbat' 1) at or around this time using A/D 74, which measurement is enabled by signal ENbat, as described in further detail later. Even though the switching circuitry 102 is opened, the IPG circuitry can still operate normally for some period of time using charge stored on Cbat. The IPG circuitry thus continues operating by drawing on this stored charge for its power, which causes Vbat' to fall. Before Vbat' falls too far, i.e., before Cbat is unable to continue to power the IPG circuitry, Vbat' is again measured (Vbat'2). The switching circuitry 102 is then closed (Sbat=0, at the end of Tbat), thus retuning Vbat' to Vbat, and thus allowing the IPG circuitry to continue its normal operation.

The difference between Vbat'1 and Vbat'2, ΔVbat', correlates to the average current, Ibat(avg), drawn by the IPG circuitry during time period Tbat:

$$Ibat(avg)=Cbat*\Delta Vbat'/Tbat,$$

where Tbat and Cbat are known, and where ΔVbat' is measured. Stated differently, the average current Ibat(avg) comprises the capacitance Cbat times the rate at which Vbat' falls, which can be determined in the microcontroller 58 by dividing the difference in the measured voltages ΔVbat' by the time period between the measurements ΔT=Tbat while the switching circuitry is opened.

While Ibat(avg) can be calculated in this manner, it may be more informative, especially to a manufacturer, to represent the measured current merely as ΔVbat', or by its constituent values Vbat'1 and Vbat'2, or by rate at which Vbat' falls (ΔVbat'/Tbat), all of which are indicative of Ibat(avg). Regardless of how the current is represented, that representation can then be telemetered to an external device for review by the manufacturer. The external device can process the telemetered representations if necessary, such as by subtracting Vbat'1 and Vbat'2 to determine ΔVbat', or by factoring in known values Cbat and Tbat to determine Ibat(avg). If ΔVbat' or Ibat(avg) are above a quality threshold Vbat(th) or Ibat(th) determined by the manufacturer, the IPG 10 may be designated as faulty. Threshold Vbat(th) is discussed and used in the examples below.

Figure 5B:
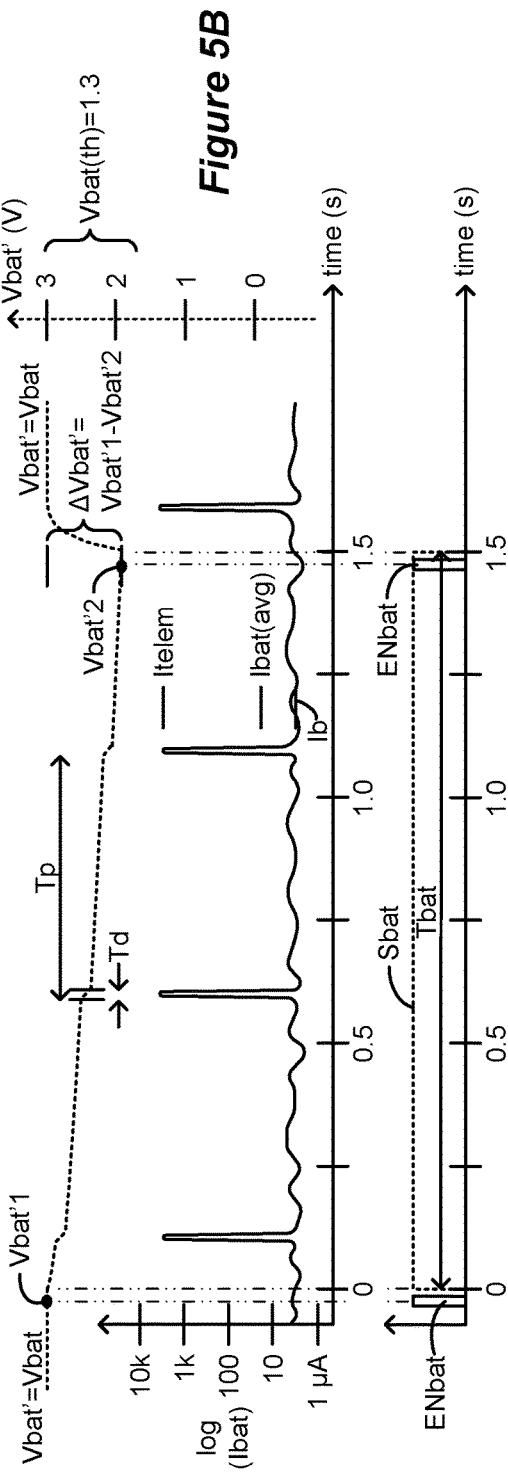

Further details of this current measurement are shown in FIG. 5B. In this example, the time period that switching circuitry 102 is opened, Tbat, equals 1.5 second, and the switch is opened at t=0 (Sbat=1). Note that Tbat, as established by signal Sbat, is chosen in light of the value of Cbat and the expected average current draw Ibat(avg) to provide a ΔVbat' that is significant, but not so large as to interfere with IPG circuitry operation, particularly at the end of Tbat when Vbat' would be at its lowest. Tbat is preferably also long enough to pick up deviations in Ibat, such as the telemetry-based current spikes resulting from the listening windows discussed earlier. For example, if Tbat=1.5 seconds, three current spikes will be covered (if Tp=0.5 s), and thus the currents experienced during these three spikes will be included in Ibat(avg) drawn by the IPG 10 during this time period.

As shown in FIG. 5B, A/D 74 is enabled via ENbat to measure Vbat'1 just prior to switching circuitry 102 being opened at t=0. Although difficult to show on the time scale of FIG. 5B, ENbat only enables A/D 74 for a short time period, e.g., 5 milliseconds—a significant time to accurately determine Vbat'1 by averaging a reasonable number of samples.

Switching circuitry 102 is then opened at t=0, the IPG circuitry continues to operate, and Vbat' begins to fall. When the IPG 10 is operating outside of a telemetry window (Td), and thus draws only its baseline current, Ibat=Ib, Vbat' drops relatively slowly. When the IPG 10 issues listening windows, Ibat=Itelem, which is significantly higher, and thus Vbat' falls off more sharply.

Prior to closing switching circuitry 102 at t=1.5, Vbat'2 is measured by A/D 74, as enabled via ENbat. The switching circuitry 102 is then closed, Vbat' returns to Vbat as Cbat is charged, and normal IPG operation continues. ΔVbat' or Ibat(avg) is then determined, either in the IPG 10 or at the external device, and can be compared to a quality threshold. For example, a threshold for ΔVbat' can be Vbat(th)=1.3 V, as shown in FIG. 5B. Because ΔVbat' as measured is less than Vbat(th) in FIG. 5B, the IPG 10 being tested would be deemed acceptable. The average current resulting from the integration of Ibat during this measurement may be about Ibat(avg)=25 µA for example.

Figure 3C:
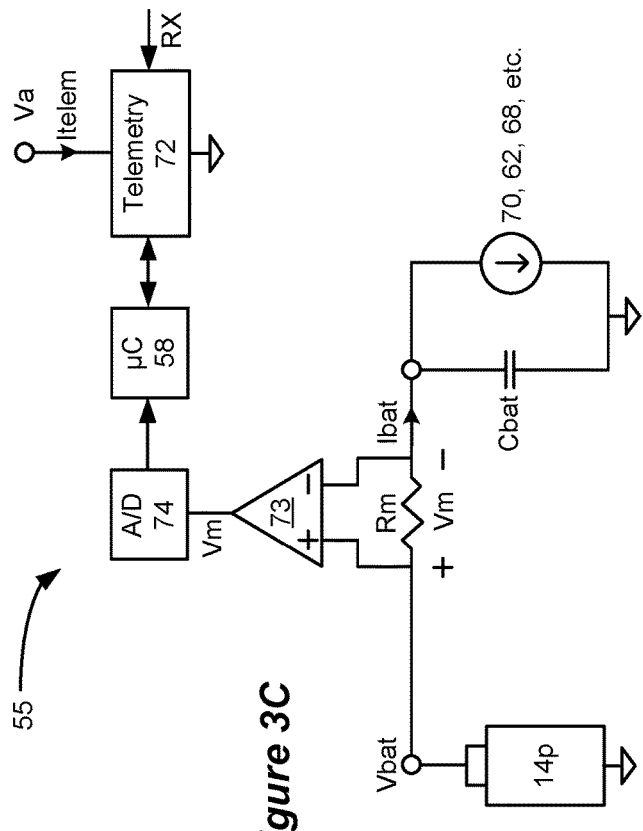
FIG. 3C shows one example of current measurement circuitry for measuring the current drawn from the battery power supply voltage.
Figure 3D:
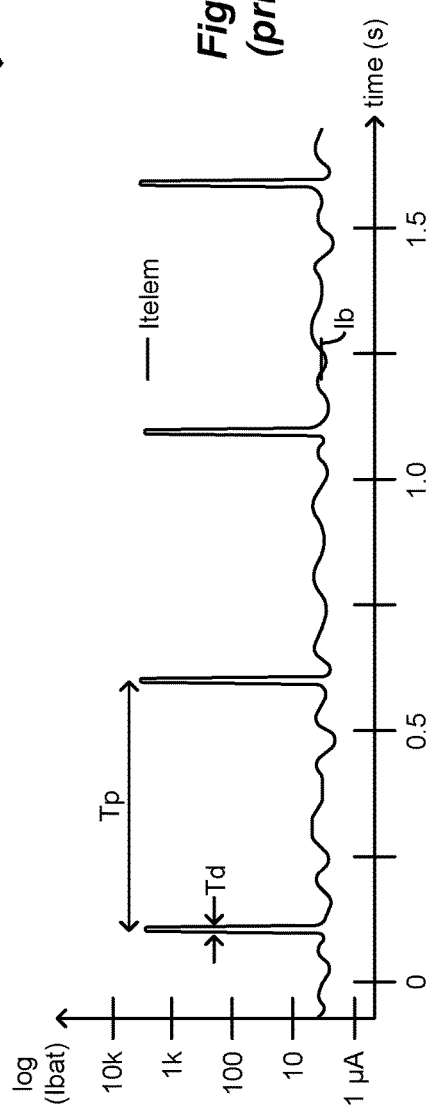
FIG. 3D shows variations in the current drawn from the battery power supply voltage in the IPG, in accordance with the prior art.

Several benefits of the current measurement circuitry 105 of FIG. 5A are apparent, particularly when compared to the current measurement circuitry 55 of FIG. 3C described earlier. First, no measuring resistor Rm or high-dynamic-range differential amplifier 73 (FIG. 3C) are required. Although A/D 74 is used in the current measurement circuitry 105 of FIG. 5A, it does not need to be used continuously during the measurement, as occurs in FIG. 3C. Instead, A/D 74 is only used to measure Vbat' at two points in time, and because Vbat' doesn't change significantly over the short duration of these measurements, such measurements can occur quickly and at rates normally used by A/D 74 to sample other voltages in the IPG 10. The measurement of Ibat thus requires only a small amount of data easily handled by the IPG 10. Any perturbations in Ibat, even if of very small duration (e.g., 1 microsecond or less), are not at risk of being missed, as any deviation in Ibat occurring during Tbat will necessarily draw charge from Cbat and thus will increase ΔVbat' and be captured in the measurement. Finally, despite disconnecting battery 14p from the IPG circuitry, the measurement of Ibat occurs without interfering with normal IPG operation, and in a manner that doesn't overtax the IPG and skew the Ibat measurement.

Figure 6C:
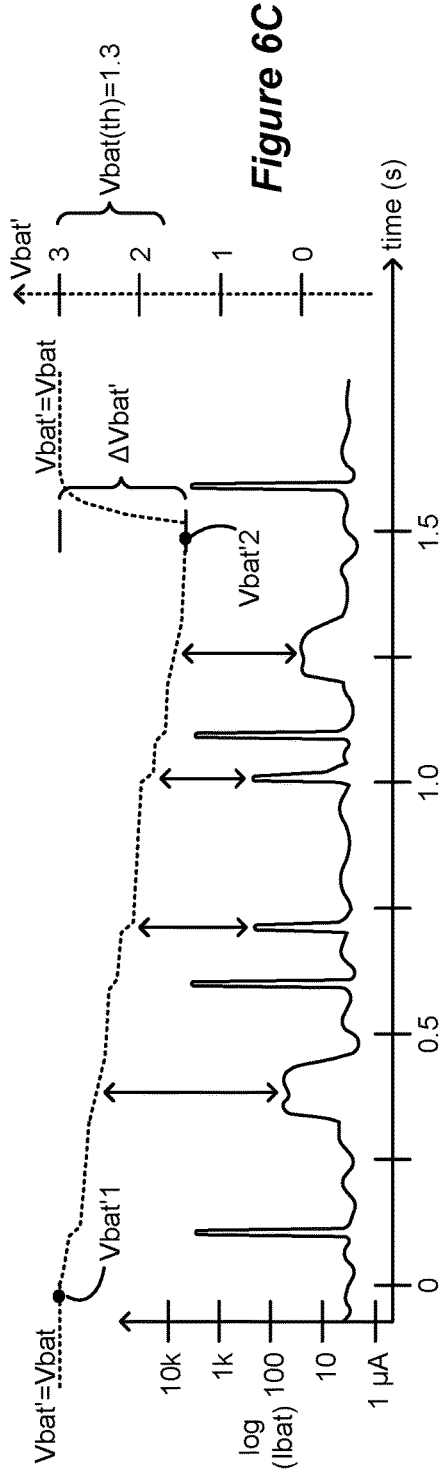

FIGS. 6A-6C illustrate different leakage currents that cause Ibat, and hence Ibat(avg), to be high in the IPG 10, which leakage currents are captured by current measurement circuitry 105. In FIG. 6A, the baseline current Ib is too high, and thus Vbat' falls off too quickly between the listening windows (Td). The telemetry current, Itelem, is however normal during the listening windows and Vbat' falls off at expected rates during these periods. Nonetheless, the resulting ΔVbat' is larger than the acceptable threshold Vbat(th) by virtue of the excessive baseline current. In FIG. 6B, the telemetry current Itelem is too high, perhaps suggesting current leakage in telemetry circuitry 72, and Vbat' thus falls off too quickly during the listening windows (Td), although the baseline current Ib is normal. Again, the net result is a ΔVbat' that is too high compared to threshold Vbat(th). In FIG. 6C, the telemetry and baseline currents are generally normal, but certain perturbations in Ibat are present, as denoted by the arrows, presumably due to some defect in the circuitry. These perturbations cause unexpected drops in Vbat', again resulting in a ΔVbat' that is unacceptable.

While it is preferable to measure Vbat' just prior to changing the status of the switching circuitry 102 (i.e., before opening at t=0 and before closing at t=1.5), this is not strictly necessary, and the voltages used to compute ΔVbat' can be measured at other times. For example, Vbat'1 can be measured via ENbat substantially before switching circuitry 102 is opened at t=0. In fact, if Vbat is periodically determined as a matter of course during normal operation of the IPG 10 (when the switching circuitry 102 is closed), then a distinct Vbat'1 measurement by current measurement circuitry 105 may not be necessary, as a most-recent value of Vbat can be used instead for Vbat' 1.

Additionally, if Vbat'1 is reasonably known, it may not need to be measured at all. For example, new IPGs under test may in some circumstances have reliable starting values of Vbat, and thus such value can simply be used for Vbat'1 when determining ΔVbat'. In other words, only Vbat'2 is measured and is subtracted from the known value for Vbat'1 (i.e., Vbat) to determine ΔVbat', thus allowing the rate of decline of Vbat' (ΔVbat'/ΔT), and Ibat(avg), to be determined. In short, it is only necessary in some implementations that measurement circuitry 102 measure Vbat' once while it falls and while the switching circuitry 102 is opened.

Figure 7:
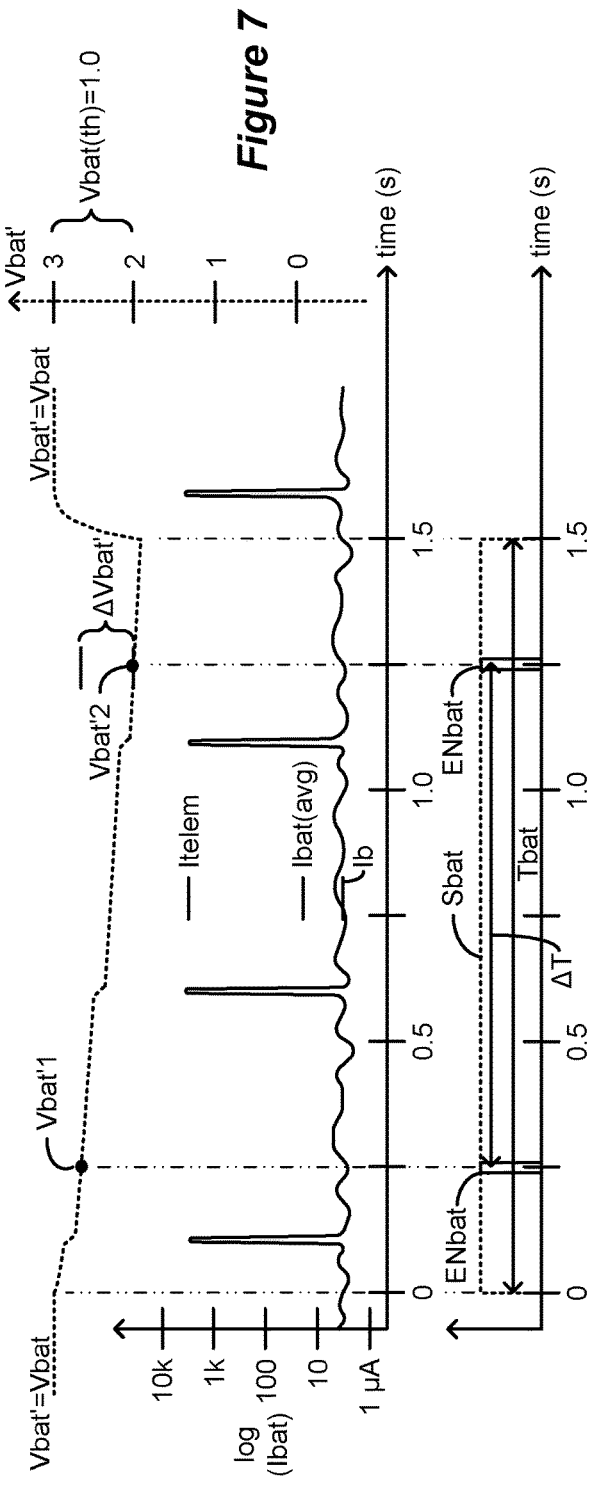
FIG. 7 shows different timings for the voltage measurements in accordance with an embodiment of the invention.

Vbat'1 can also occur significantly after switching circuitry 102 is opened at t=0, as shown in FIG. 7. Here, Vbat'1 is measured at t=0.25 after the switching circuitry 102 has been opened at t=0 and Vbat' has begun to fall. Likewise, Vbat'2 is measured at t=1.25 significantly before switching circuitry 102 is closed at t=1.5. ΔVbat' in this instance correlates to Ibat using a different, smaller time period, ΔT (1.25−0.25=1.0 second), between the two measurements, i.e., $$Ibat(avg)=\Delta Vbat'*Cbat/\Delta T,$$

A smaller quality threshold, Vbat(th) (e.g., 1V), would be used in this instance to account for the smaller time period ΔT between the two measurements.

It should be remember that the relevant time period ΔT for determining the rate at which Vbat' falls—i.e., that which is proportional to load current Ibat(avg)—comprises the time period between the measurements but only while the switching circuitry 102 is opened. This is not an issue in FIG. 7, as both measurements Vbat'1 and Vbat'2 are taken while the switch is opened, and thus ΔT simply comprises the difference between those measurements. However, if Vbat'1 is measured far in the past, for example at t=−10 s perhaps during the IPG's routine monitoring of Vbat, such time before the switching circuitry 102 is opened is not included in ΔT. For example, if in this scenario the switching circuitry 102 is opened at t=0, and Vbat'2 is measured at 1.25 s, the relevant time period reflective of the rate of decline of Vbat' is ΔT=1.25 s, not 11.25 s. In short, the relevant time period ΔT need not be defined by the times the Vbat' measurements are taken.

Figure 8:
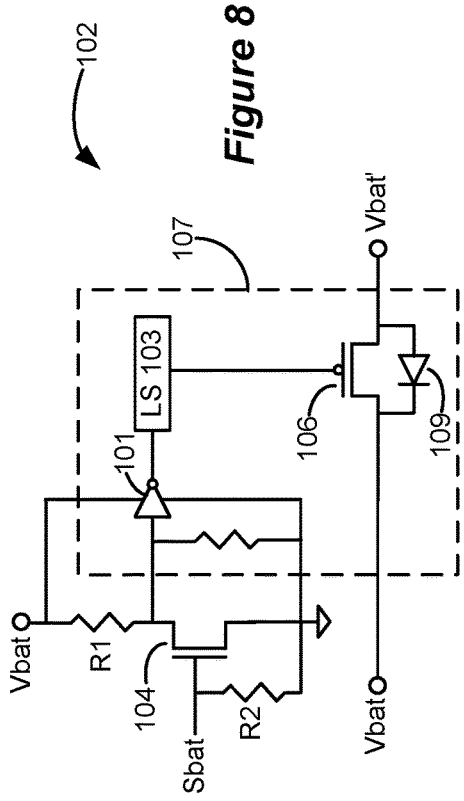
FIG. 8 shows further details of the switching circuitry, in accordance with an embodiment of the invention.

FIG. 8 shows further details of one example of the switch circuitry 102. Ultimately, the battery (Vbat) and the IPG circuitry (Vbat') are connected or disconnected by a P-channel transistor 106 in this example. Transistor 106 can comprise a component in a high-side power switch 107 such as Part Nos. ADP190/ADP191, manufactured by Analog Devices, Inc., which additionally includes an inverter 101, a level shifter 103, and a diode 109. Use of these parts is preferred because they provide low on resistances (about 0.1 ohms), are small, and draw little power. Added outside of 107 are an N-channel transistor 104 and pull up and pull down resistors R1 and R2, which are preferably large (e.g., 1 Mohm) to preserve power. These additional components are preferred to ensure that the battery 14p (Vbat) connects to the IPG circuitry (Vbat') by default, even when the IPG 10 is first powered. In this case, R2 pulls Sbat to ground (Sbat=0) to ensure that transistor 104 is off, and R1 pulls the input of inverter 101 high, which will in turn pull (though level shifter 103) the gate of transistor 106 low, thus closing the transistor 106 and connecting Vbat' to Vbat. When Sbat is asserted to take the disclosed measurements (Sbat=1), transistor 104 turns on, passing ground to the input of the inverter 101 and dominating pull up resistor R1. Inverter 101 thus pulls (though level shifter 103) the gate of transistor 106 high, thus opening that transistor and disconnecting Vbat' from Vbat. Switching circuitry 102 of FIG. 8 however is just one example, and simpler circuits can be used. For example, Sbat can be provided directly to the input of the inverter 101, or can be provided to the gate of a single transistor such as 106. Although Sbat is active high to open the switching circuitry 102 during the current measurement, it may be active low in other examples.

Figure 9A:
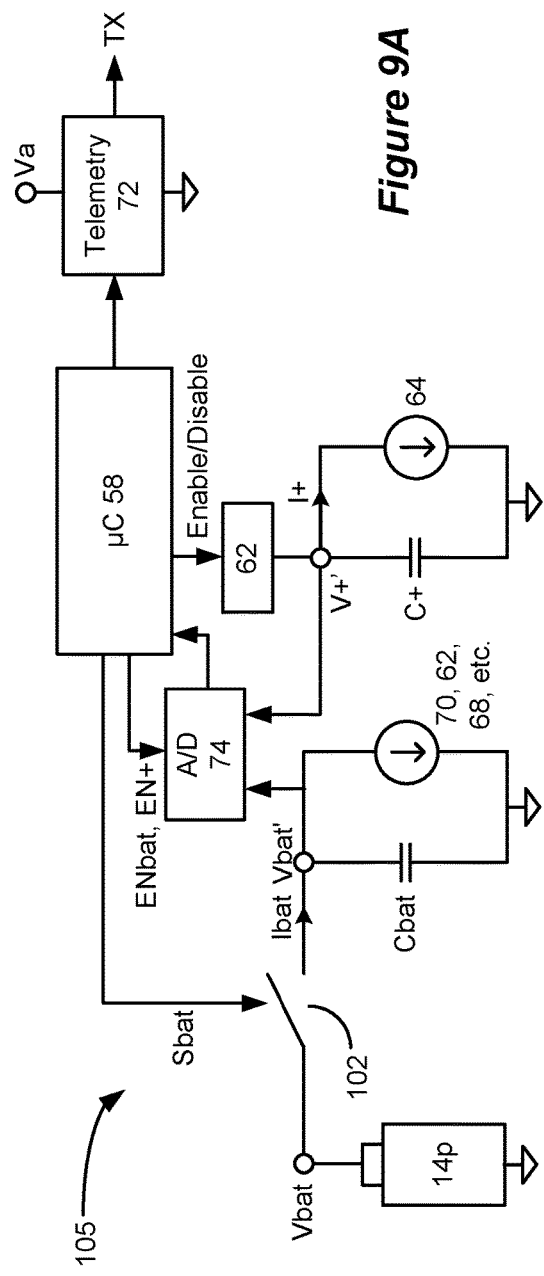
FIGS. 9A and 9B show simultaneous measurement of the current drawn from the battery power supply voltage and the current drawn from a compliance power supply voltage, in accordance with an embodiment of the invention.

As noted earlier, the inventors desire the ability to determine current draws from particular power supplies (aside from the main power supply Vbat), to narrow down which circuits in the IPG 10 might be drawing excess current. Current measurement circuitry 105 is adaptable to make such measurements. For example, as shown in FIG. 9A, in addition to measuring the current draw (Ibat) from the main power supply voltage Vbat as before, current measurement circuitry 105 is also configured to simultaneously determine the current draw (I+) from the V+ power supply voltage, i.e., that provided by DC-DC converter 62 (FIG. 4) to power the DAC(s) 64 to generate therapeutic pulses. In this regard, note that a capacitance C+ appears in parallel with power supply voltage V+', which could comprise capacitances inherent in the output of the converter 62 and the input of the DAC(s) 64, but which would likely primarily comprise intentional capacitance added to filter and stabilize V+.

Figure 9B:
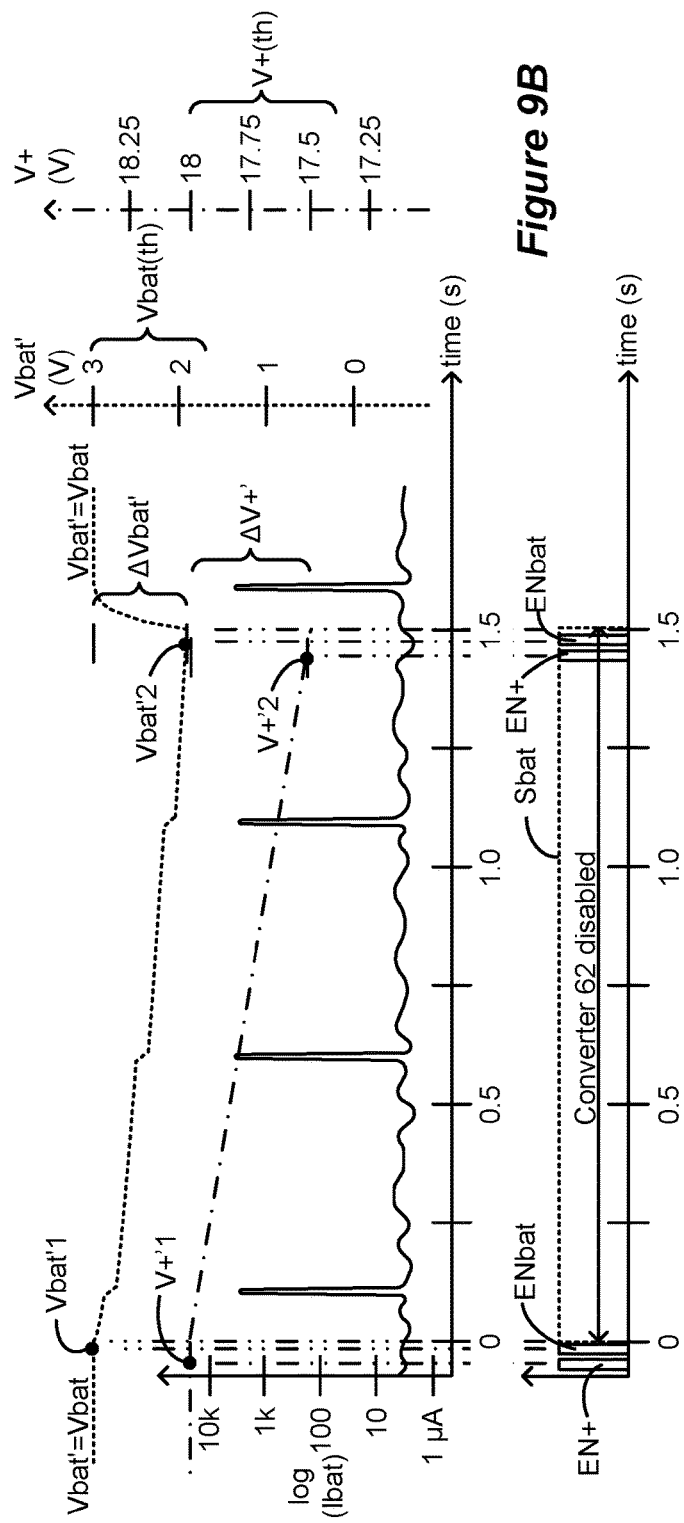

As shown, A/D 74 receives both Vbat' and V+' as inputs, and time multiplexes their measurements using enable signals ENbat and EN+, as shown in detail in FIG. 9B. In this example, prior to t=0, the microcontroller 58 has instructed DC-DC converter 62 to generate a maximum voltage for V+ of 18V. EN+ is activated to measure V+'1, followed by activation of ENbat to measure Vbat'1. The switching circuit 102 is then opened as before (Sbat=1) at t=0. Additionally, the microcontroller 58 disables converter 62 (S+=1), which allows V+' to fall in accordance with C+ and current I+ drawn therefrom. V+' as depicted will drop smoothly, as current I+ should not experience significant variance, and remains at a significant value during the measurement to allow the DAC(s) 64 to produce current pulses without interruption. The enable signals EN+ and ENbat are again activated to measure V+'2 and Vbat'2 towards the end of time period Tbat, and the switching circuitry 102 is again closed and converter 62 enabled (Sbat=S+=0) at t=1.5. ΔVbat' and ΔV+' can then be computed (either in the IPG or the external device) to determine Ibat(avg) (as discussed above) and I+(avg), where $$I+(avg)=\Delta V+'*C+/Tbat.$$

ΔVbat' and ΔV+' may also be compared to thresholds Vbat(th) and V+(th) to make quality determinations whether Ibat and I+ are too high. Threshold V+(th) may be set to 0.55 V in this example.

While FIGS. 9A and 9B illustrate the convenience to determining Ibat and I+ simultaneously, note that I+ could also have been determined by itself, without disconnecting Vbat at switching circuitry 102. Instead, the microcontroller 58 could simply temporarily disable the DC-DC converter 62 (e.g., S+=1 from t=0 to 1.5), preventing it from further generating power supply voltage V+, and allowing V+' to fall to permit the I+ measurement to be made.

Figure 9C:
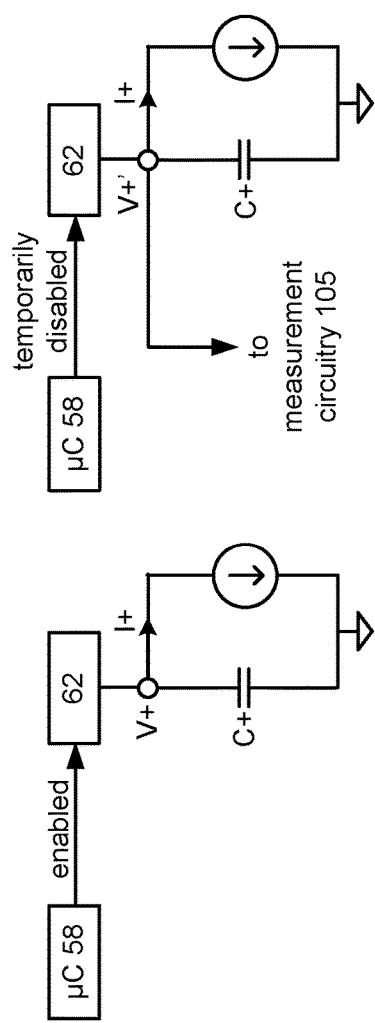
FIG. 9C shows use of the current measurement circuitry without the use of switching circuitry, instead relying on disabling the circuit that generates a power supply voltage, in accordance with an embodiment of the invention.

This example shows that the use of additional switching circuitry 102 is not necessarily required to measure current per the disclosed technique, and to isolate a current drawing load from its power supply. As shown in FIG. 9C, if a circuit (such as DC-DC converter 62) that generates a particular power supply (e.g., V+) can be disabled, such disabling for a temporarily time period may effectively operate to disconnect the load (V+') from its power supply without the need for switching circuitry 102. Indeed, disabling a power-supply generating circuit block may actually involve opening a switch to disconnect that block from its power supply, in which case this built-in disabling switch is in effect used like the switching circuitry 102 disclosed.

Although not shown in FIG. 9C, the boost converter 70 in the IPG 10 can also be similarly enabled and disabled by the microcontroller 58, thus allowing the current drawn from power supply voltage Vup (i.e., Iup) to be measured via Vup'1 and Vup'2 over a time period Tup. In another example, if it was desired to measure Id being drawn from power supply voltage Vd, it would be necessary to either temporarily disable the regulator 46 that produces Vd, or the boost converter 70 upstream that provides Vup to the regulator 48. However, it cannot be assumed in these examples that these power supply voltages can necessarily be disabled for the same time period as Vbat described earlier (Tbat). This is because the load circuits connected to each power supply voltage will have their own capacitances that will determine how quickly the voltage at that power supply will fall off given the current being drawn.

Figure 10A:
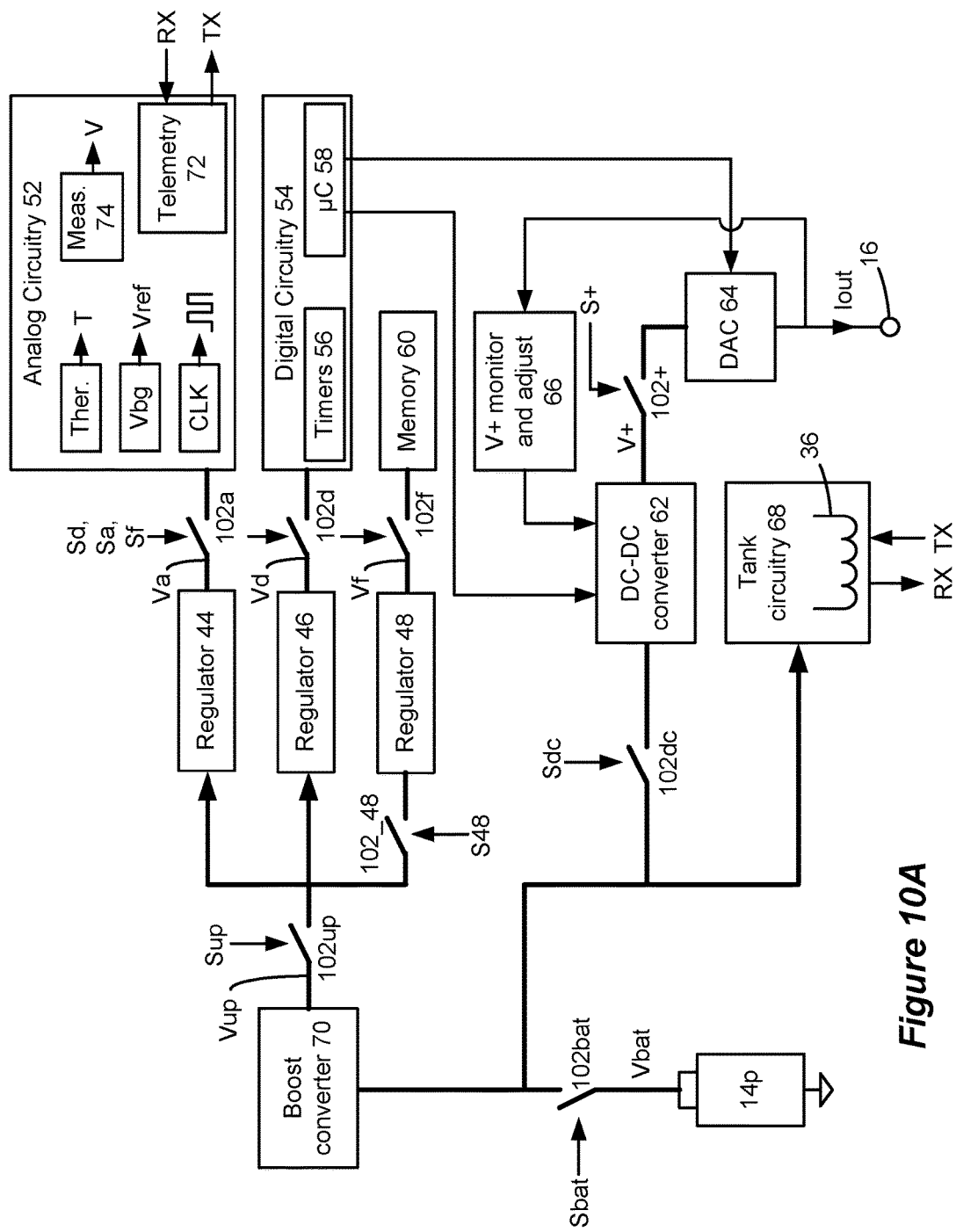
FIGS. 10A-10D show modification of the current measurement circuitry to include a number of switching circuitries for measuring a plurality of currents drawn from a plurality of power supply voltages in the IPG, in accordance with an embodiment of the invention.
Figure 10B:
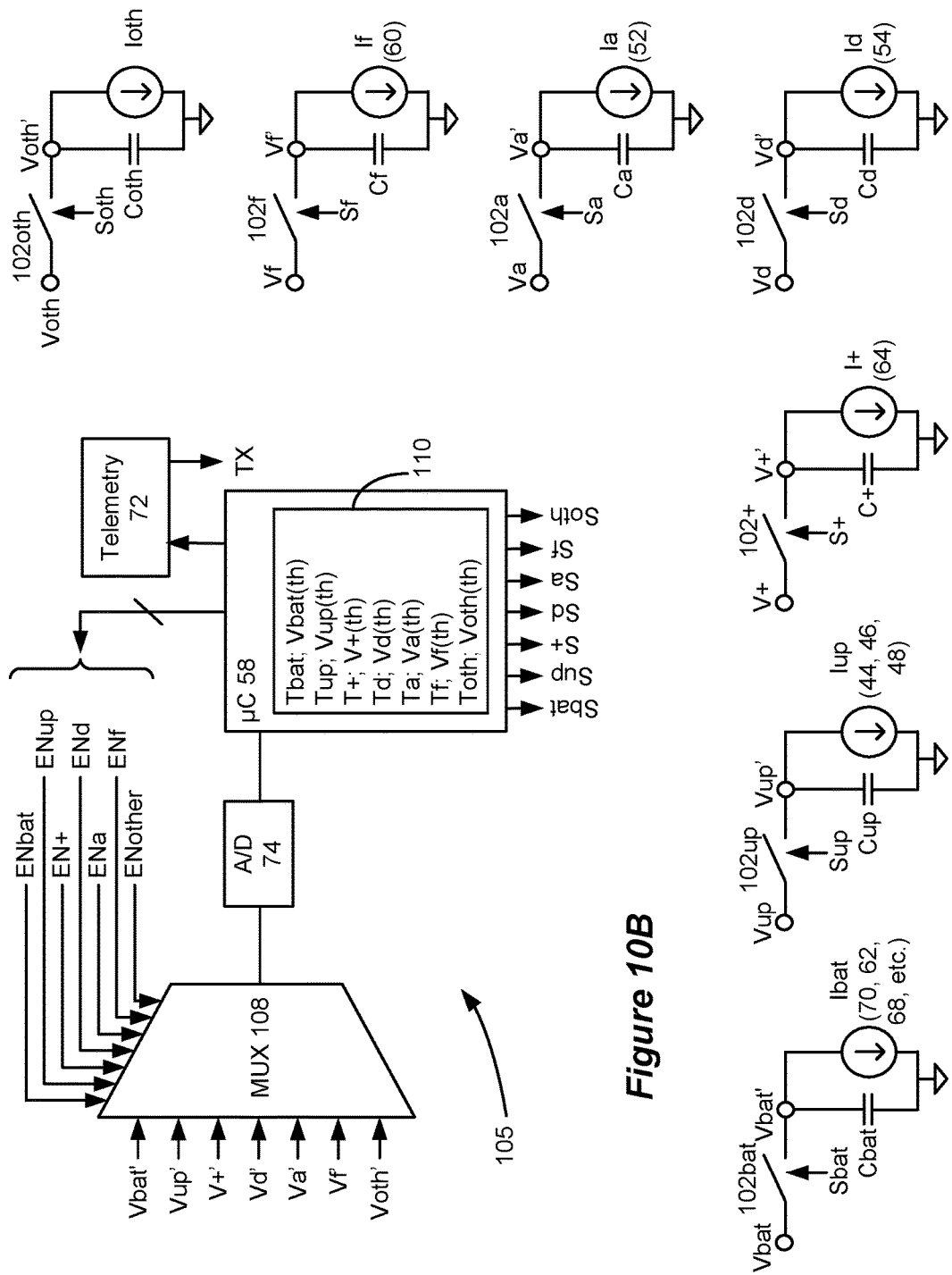
Figure 10C:
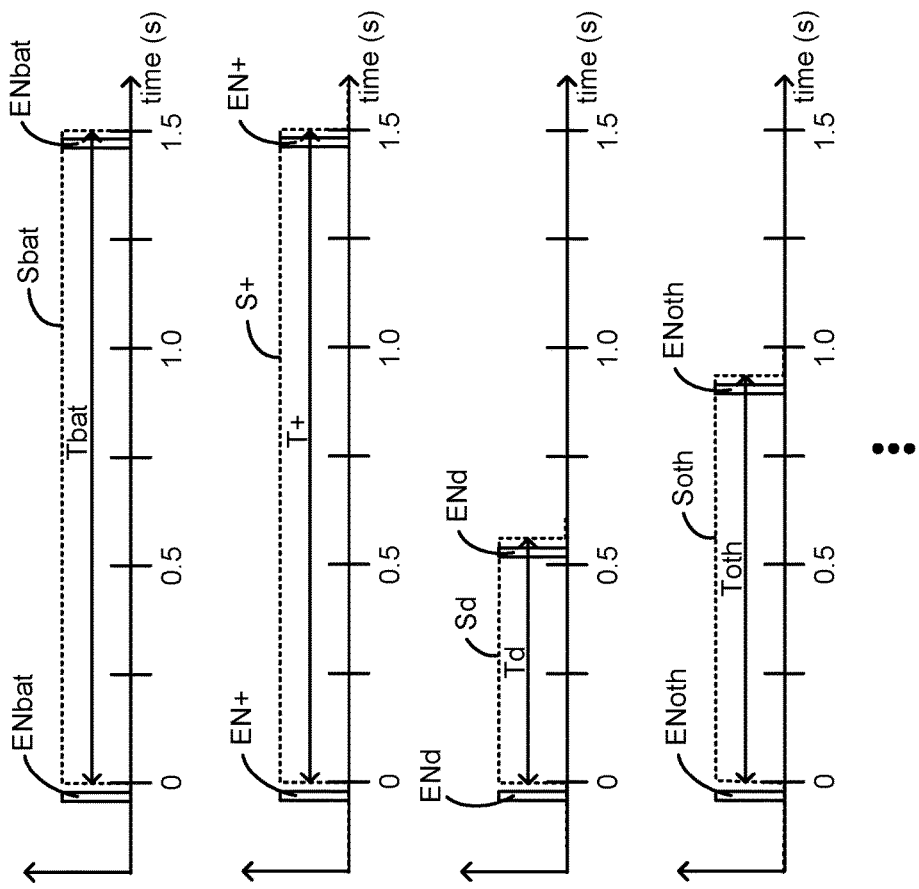

FIGS. 10A-10C provide a comprehensive solution in which current measurement circuitry 105 is scaled such that each power supply voltage (Vbat, Vup, Va, Vd, Vf, V+) is provided with its own switching circuitry (102bat, 102up, 102a, 102d, 102f, 102+), enabling the independent or simultaneous measurement of the current drawn from each of these supplies (Ibat, Iup, Id, Ia, If, I+ respectively). Additionally, some branches of these power supply voltages are provided with switching circuitry 102 to assess currents being drawn just from those branches. For example, as shown in FIG. 10A, the power supply voltage to DC-DC converter 62—a branch of Vbat—is provided with switching circuitry 102dc which allows just the current of the converter 62 (Idc) to be determined. Likewise, the power supply voltage to regulator 48—a branch of Vup—is provided with switching circuitry 102_48 which allows just the current of that regulator (I48) to be determined. Other power supply voltages (Voth), or their branches, or indeed any voltage in the IPG 10 whose current draw is desirable to know, can likewise be provided with their own dedicated switching circuitries 102.

It should be noted that certain switching circuitries 102 depicted in FIG. 10A may already be present in a given IPG 10, and thus such pre-existing switches need only be suitably controlled by the microcontroller 58, and connected to the current measurement circuitry 105 in accordance with the disclosure technique. As already noted, this may be the case for the boost converter 70 and DC-DC converter 62. Other circuits in IPG 10 may likewise already have suitable switching circuitries that can be used as well. In short, implementation of the disclosed current-measuring technique to multiple power supplies may not necessarily require the addition of switching circuitry 102 to every power supply of interest. Nonetheless, it will be assumed for simplicity in the depicted examples that a discrete switching circuitry 102 is used for each power supply.

As shown in FIG. 10B, the microcontroller 58 in the IPG is programmed (110) with the time periods Tx that the various switching circuitries 102x should be opened via respective control signals Sx to permit the measurement of the current draws from associated power supply voltages Vx. Again, such time periods Tx will depend on the capacitance Cx inherent or intentionally provided at the various power supplies. Tx is preferably determined to allow circuits drawing from power supply voltage Vx to continue to do so without interruption, and without ceasing operation because such circuits are not receiving acceptable power. For example, if the capacitance Cd at power supply voltage Vd is relatively large, and if the expected current draw Id is relatively small, the measurement time Td with which switching circuitry 102d should be temporarily opened using signal Sd may be relatively large. If desired, and if it would not interfere with operation of the IPG 10, Cx can be changed for a particular load circuit to facilitate measuring the current Ix. For example, if the capacitance Cf at power supply voltage Vf is relatively small, and if the expected current draw Id is relatively large, capacitance Cf can intentionally be increased to decrease the rate at which Vf declines when disconnected, thus allowing the time period Tf during which If is measured (Vf1, Vf2) to be increased.

Additionally, enable signals ENx that determine when various voltages Vx' should be measured can be associated with, or determined based on, the values Tx stored in the microcontroller 58, such that the microcontroller 58 can issue measurement enable signals ENx and switch control signals Sx at appropriate times. For example, if microcontroller 58 knows Tx for a given power supply voltage, and when called on to assert Sx to temporarily disconnect power supply voltage Vx to measure its current Ix, it can assert enable signal ENx just prior to the assertion of Sx (when switch 102x is opened) to enable A/D 74 to measure Vx'1, and again just prior to deasserting Sx (when switch 102x is again closed) to measure Vx'2. However, as described earlier, the measurements of Vx'1 and Vx'2 needed to determine ΔVx' and hence Ix need not occur just prior to a state change of the switching circuitry 102x, and thus microcontroller 58 can assert ENx at different times in accordance with Tx (see, e.g., FIG. 7). FIG. 10C shows examples of different timings at which the various switching circuitries 102x can be controlled, given the particular time periods Tx suitable for each power supplies' current measurement.

As shown in FIG. 10B, a multiplexer 108 can be used to control which power supply voltage Vx is being measured by A/D 74 at any given time in accordance with enable signals ENx, and the microcontroller 58 can arbitrate issuance of the enable signals ENx to ensure that only one voltage is measured at a time. Note that multiplexer 108 may very well have additional inputs to allow A/D 74 to measure other voltages in the IPG, and that sample and hold circuitry can be used to stabilize such voltages prior to presentation to A/D 74. See, e.g., U.S. Patent Application Publication 2012/0095529.

Current measurement circuitry 105 of FIGS. 10A-10C thus permits the current Ix at any power supply voltage Vx to be measured at any time without interfering with IPG 10 operation. If desired, and as shown in FIG. 10B, the microcontroller 58 can also be programmed (110) with thresholds Vx(th) to allow quality determinations to be made concerning the various currents Ix, as described above. The ability to determine the various current Ix at various power supplies Vx is again beneficial, because it can inform as to where in the IPG's circuitry current leakage may be occurring.

Measuring a particular current Ix can occur on demand, such as by the manufacturer wirelessly sending a command for a particular measurement from a user interface of an external device. Alternatively, the microcontroller 58 can be programmed to measure one or more of currents Ix automatically, which currents Ix (ΔVx') can be stored and later transmitted to the manufacturer to understand how current Ix might be varying over time.

Additionally, because the disclosed current measuring technique does not interfere with IPG operation, such measurements can continue to be made even after the IPG 10 has been implanted in a patient. Thus a patient can also command certain currents Ix to be measured, or review them if automatically taken and stored by the IPG 10, using a graphical user interface of his patient external device, such as is disclosed in various forms in U.S. Pat. No. 9,186,518, which is incorporated herein by reference.

Figure 10D:
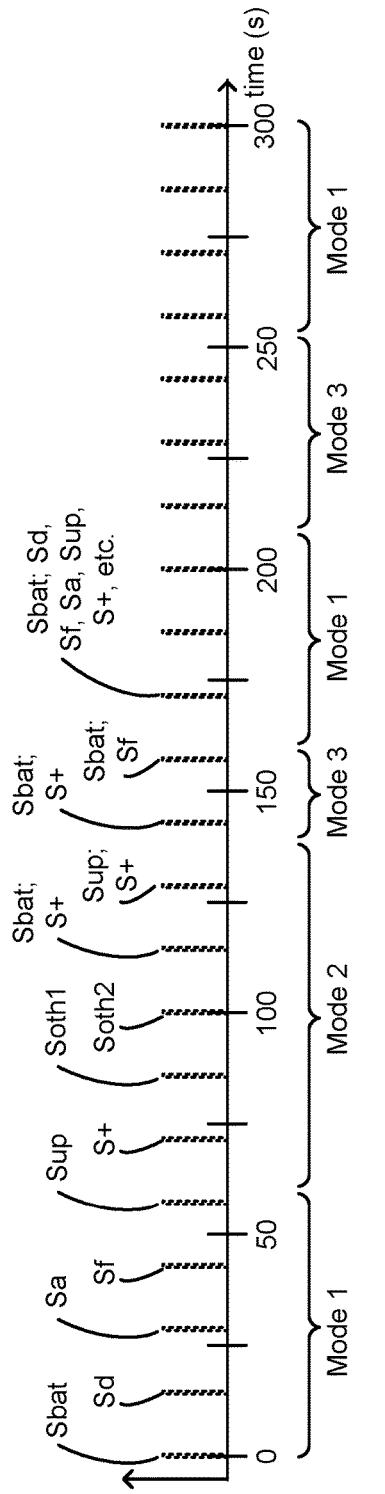
Figure 10D:
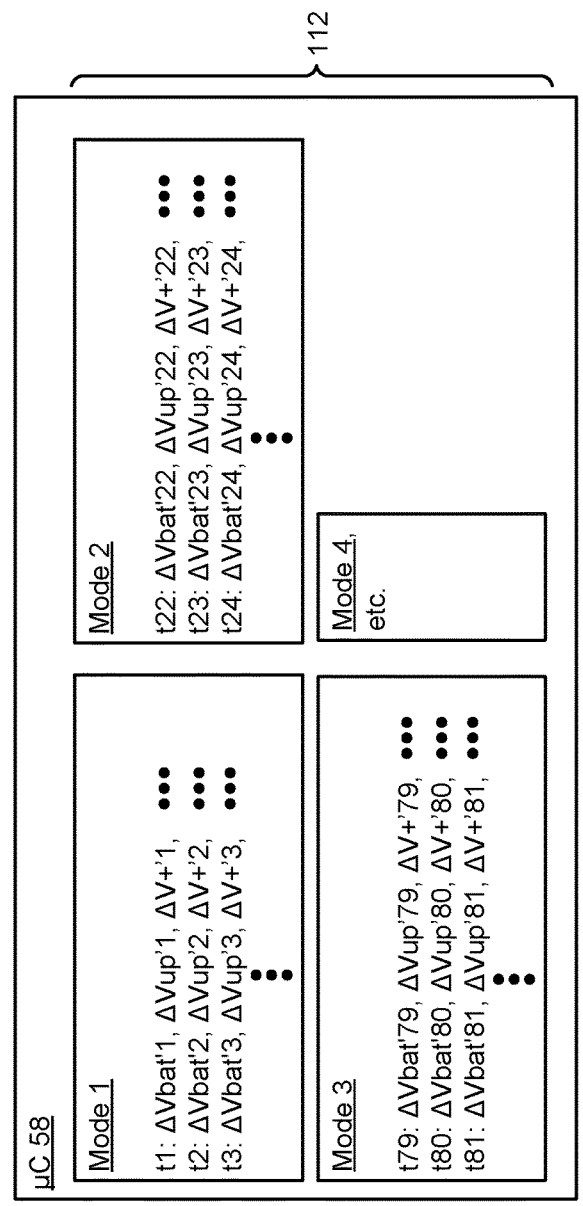

FIG. 10D shows automatic monitoring of one or more of currents Ix in the IPG 10 for benefit of either the patient or the manufacturer. In this example, the microcontroller 58 is programmed to take and store (112) one or more measurements at periodic intervals, such as every 15 seconds or so. As shown, single current measurements can be made at these intervals, and as shown individual control signals Sx are asserted during the first eight intervals to measure Ibat (ΔVbat'), Id (ΔVd'), Ia (ΔVa'), If (ΔVf'), Iup (ΔVup'), I+(ΔV+') and two other currents of interest (Ioth1, Ioth2). Later intervals measure more than one current simultaneously, although it should be remembered that the control signals Sx may be asserted for different amounts of time given the different time periods Tx appropriate for each power supply voltage Vx. A final interval measures all of the currents, and thus all control signals are asserted. While such control signals Sx may overlap in this instance, the microcontroller 58 would likely need to arbitrate the issuance of the various switch control signals Sx and their associated measurement enable signals ENx to ensure that A/D 74 measures only one voltage at a time. (Additional A/D circuits 74 could also be provided for each power supply measurement if desired). In short, the measurements taken at each interval can comprise one, some, or all of the currents at the power supply voltages Vx, or at other voltages of interest. Alternatively, the various currents could be measured at different intervals, with currents of greater interest being measured with greater frequency.

The measured currents ΔVx' (or Vx' 1 and Vx'2, or Ix(avg), depending on the processing), are then stored (112) for later transmission to the manufacturer, clinician, or patient for review at their external devices. Such stored values are preferably also provided with time stamps (tx) to allow the currents to be reviewed as a function of time if necessary. As shown in FIG. 10D, measurements ΔVx' are provided at each of the time stamps for each of the power supplies, although as just noted not all currents for every power supply may be measured at every interval.

Additionally, an IPG 10 may operate in more than one mode, with different modes affecting the various currents in different ways. Accordingly, microcontroller 58 may additionally store information pertaining to the mode at the time of the measurements to allow for review of the currents as a function of mode as well as time.

Figures 11A, 11B:
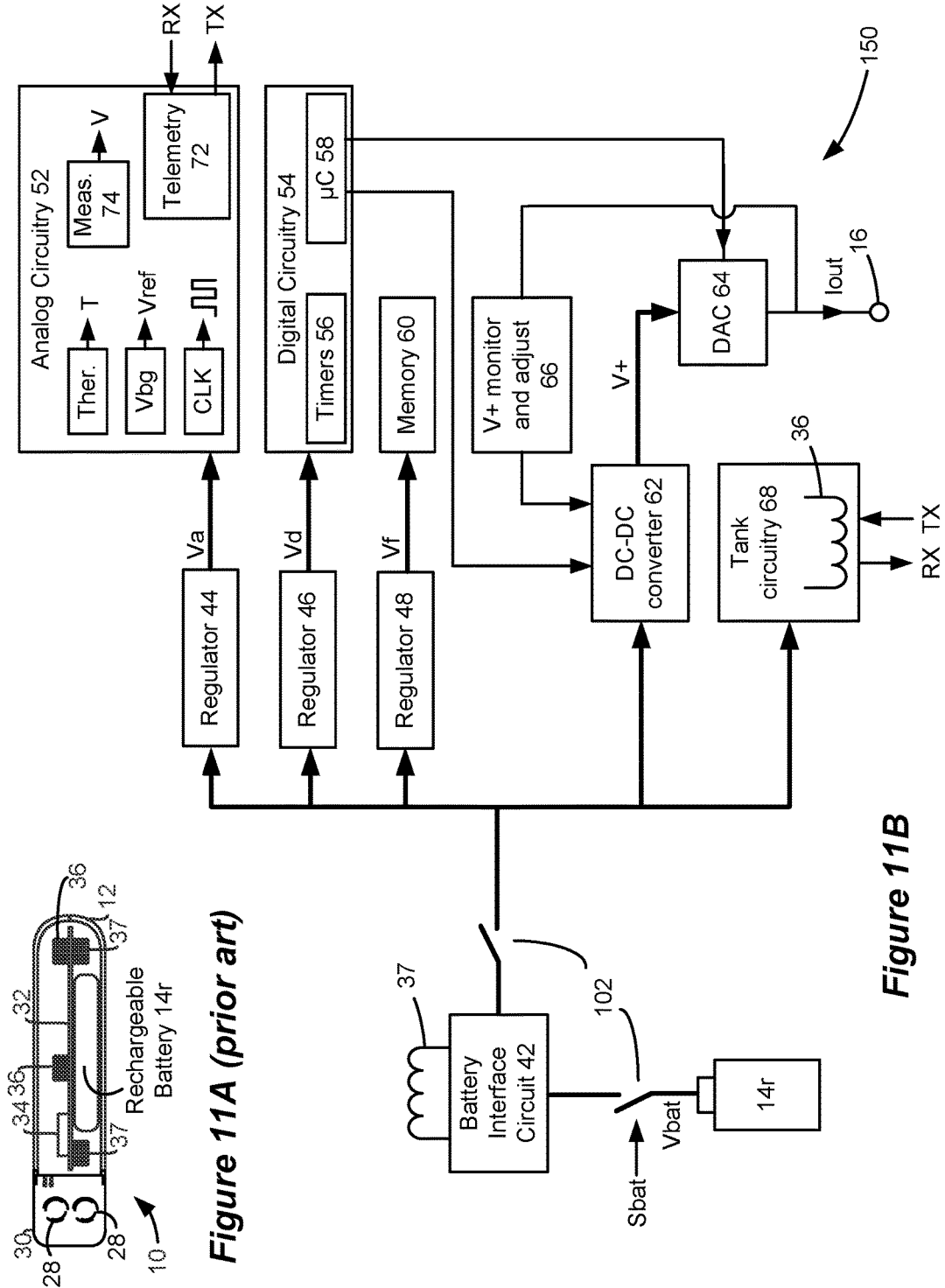
FIGS. 11A-11C show application of the disclosed current measurement circuitry to an IPG with a rechargeable battery, in accordance with an embodiment of the invention.

The disclosure to this point has focused on the use of current measurement techniques with IPGs 10 having primary batteries 14p. However, the technique is not so limited, and can be used in IPGs 10 with rechargeable batteries 14r as well, such as shown in FIG. 11A. Rechargeable batteries 14r can be formed using different chemistries, but lithium ion polymer batteries are popular for use in implantable medical devices, and can be charged to a battery voltage of about Vbat_max=4.2 Volts in one example. The battery voltage, Vbat, of rechargeable battery 14r will fall as it is used, and is preferably recharged at around Vbat=2.5 Volts to ensure proper IPG operation.

As shown, the rechargeable-battery IPG 10 of FIG. 11A includes an additional charging coil 37, although in other examples telemetry coil 36 may also function as a charging coil. As is well-known, and referring to FIG. 11C, which is largely reproduced from U.S. Patent Application Publication 2013/0023943, charging coil 37 receives a magnetic charging field from a coil in an external device such as a hand-holdable and portable external charger (not shown). This magnetic charging field induces an AC current in charging coil 37, which is rectified 45 to a DC level and used to recharge the battery 14r using battery interface circuitry 42.

Battery interface circuitry 42 protects rechargeable battery 14r from being overcharged to too high a voltage (an overvoltage condition, OV), and can also intentionally discharge the battery 14r (144) if necessary. Battery interface circuitry 42 can also disconnect the battery 14r from the remainder of the IPG circuitry (Vbat') via transistors 102a and 102b, which are wired in parallel. Switches 102a and 102b are controllable in the '943 Publication to disconnect the IPG circuitry if too much current Ibat is being drawn (an over current condition, OI), if the battery voltage Vbat falls too low (an undervoltage condition, UV), or if the IPG needs to be shut off in an emergency, such as upon detection of a magnetic field provided by an external bar magnet (μ). Further details concerning operation of battery interface circuit 42 can be found in the '943 Publication, and some elements numbers from that publication are used in FIG. 11C.

Figure 4:
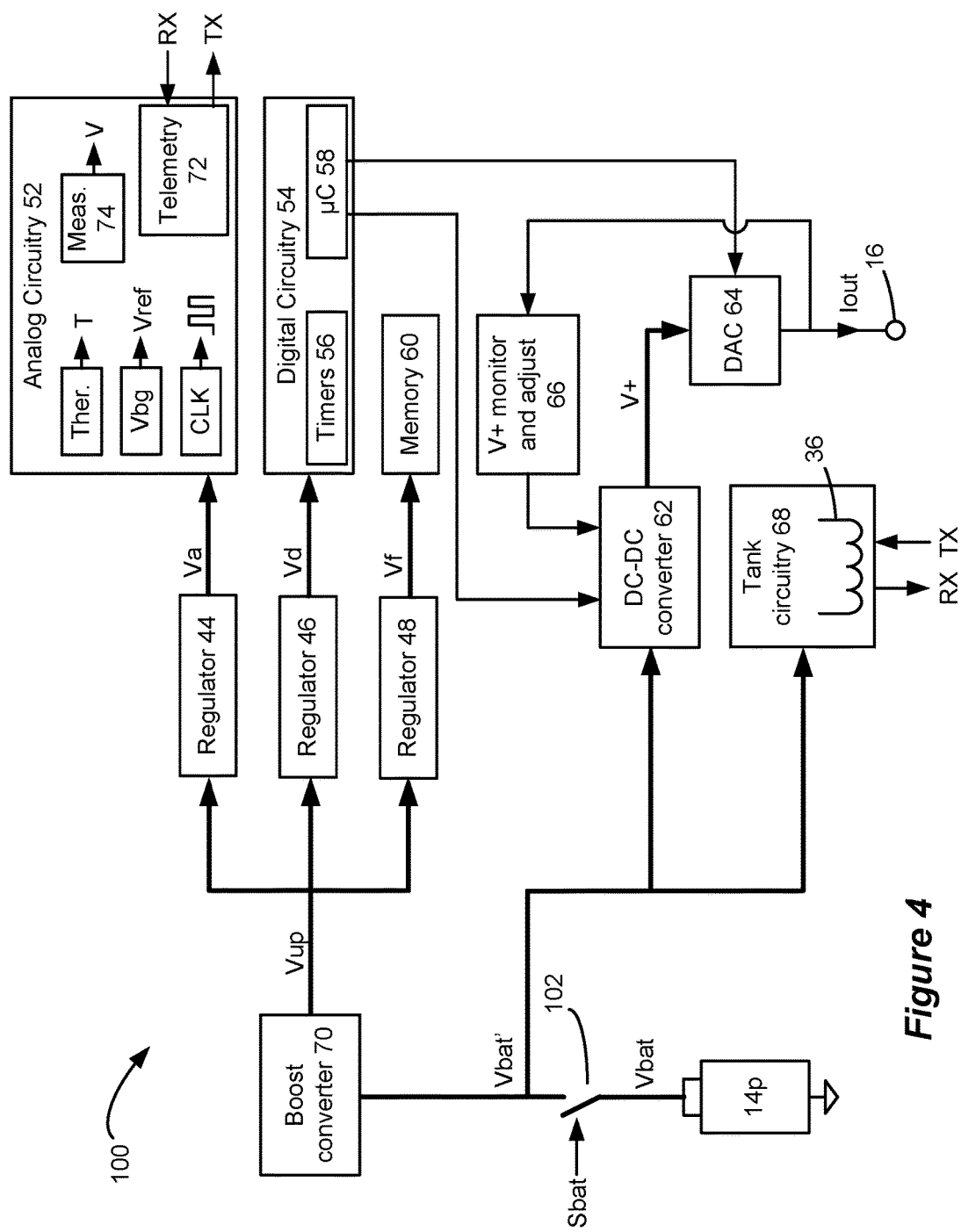
FIG. 4 shows an improved architecture for an IPG having current measurement circuitry including switching circuitry for measuring the current drawn from the battery power supply voltage, in accordance with an embodiment of the invention.

The architecture 150 for the rechargeable-battery IPG is shown in FIG. 11B, which is reproduced from the '910 Publication incorporated by reference earlier, and includes many of the same circuits and power supplies used by primary-battery architecture 100 (FIG. 4). Thus, rechargeable-battery architecture 150 is not discussed in detail. However, shown in FIG. 11B is the provision of switching circuitry 102 to measure a power supply current (in this case, Ibat), which can occur either between the battery 14r and the battery interface circuitry 42, or between the battery interface circuitry 42 and the remainder of the IPG circuitry as shown. Other switching circuitries 102 may also be provided to measure the current draws at different power supply voltages as described earlier (see, e.g., FIG. 10A), but these are not shown for convenience.

Figure 11C:
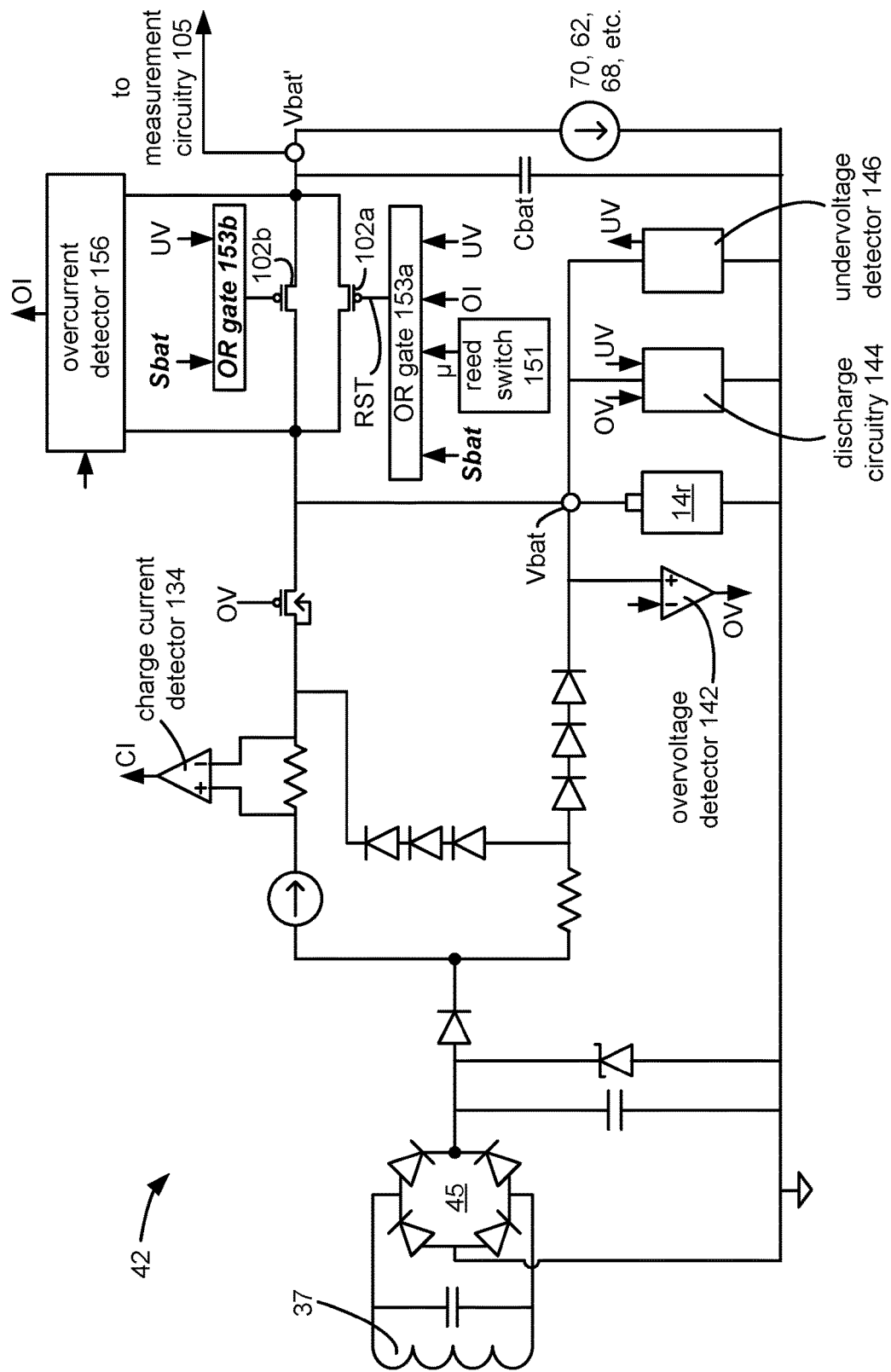

As described earlier, battery interface circuit 42 of FIG. 11C already uses switches 102a and 102b between the battery 14r and the reminder of the IPG circuitry (Vbat'), and so current measurement circuitry 105 can use these switches to measure Ibat via ΔVbat'. As shown in FIG. 11C, Vbat' is connected to current measurement circuitry 105 as disclosed earlier, and control signal Sbat is provided via OR gates 153a and 153b to control both of switches 102a and 102b in addition to other control signals OI, UV, and μ described earlier. OR gate 153b is new, and not disclosed in the '943 Publication. If it is assumed that OI, UV, and μ are low, as is typical assuming no problem with the IPG 10 that these signals are designed to indicate, and if Sbat is low because no current measurement is being taken by current measurement circuitry 105, OR gates 153a and 153b provide a low input to the gates of P-channel transistors 102a and 102b to connect Vbat to Vbat', thus allowing the IPG to operate normally to draw power from the rechargeable battery 14r. When Sbat is temporarily asserted by current measurement circuitry 105 (Sbat=1), both of OR gates 153a and 153b output a high value, which turns off transistors 102a and 102b, thus temporarily disconnecting Vbat' from Vbat as necessary for the measurement of Ibat (ΔVbat').

The disclosed current measuring techniques can be used in contexts other than implantable medical devices as well.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical device, comprising:
a power supply configured to produce a power supply voltage;
one or more load circuits configured to draw power from a first node;
switching circuitry configured when closed to connect the power supply voltage to the first node thus allowing the one or more load circuits to draw power when operating from the power supply voltage at the first node; and
control circuitry configured to infer from a voltage at the first node a load current through the one or more load circuits by opening the switching circuitry.

2. The device of claim 1, wherein the power supply comprises a battery.

3. The device of claim 1, wherein the power supply comprises a regulator circuit, wherein the regulator circuit is configured to produce the power supply voltage from another power supply voltage.

4. The device of claim 1, wherein the power supply comprises a converter circuit, wherein the converter circuit is configured to produce the power supply voltage from another power supply voltage.

5. The device of claim 4, wherein the converter circuit comprises a capacitor-based change pump, an inductor-based step-up converter.

6. The device of claim 1, wherein the control circuitry is configured to infer from the voltage at the first node an average load current through the one or more load circuits by opening the switching circuitry.

7. The device of claim 1, wherein the control circuitry is further configured to close the switching circuitry after opening the switching circuitry.

8. The device of claim 1, further comprising telemetry circuitry, wherein the telemetry circuitry is configured to wirelessly transmit a parameter indicative of the inferred load current to an external device.

9. The device of claim 8, wherein the telemetry circuitry comprises one of the one or more load circuits.

10. The device of claim 1, further comprising a capacitance in parallel with the at least one load circuit, wherein the control circuitry is configured to infer the load current using a value of the capacitance.

11. The device of claim 1, wherein the control circuitry is configured to open the switching circuitry for a time period, wherein the control circuitry is further configured to infer the load current using a value of the time period.

12. The device of claim 1, wherein the control circuitry is further configured to measure the voltage at the first node at least once while the switching circuitry is opened.

13. The device of claim 12, wherein the control circuitry further comprises an Analog-to-Digital converter configured to measure the voltage at the first node.

14. The device of claim 12, wherein the control circuitry is configured to infer the load current by measuring an amount the voltage at the first node falls, or a rate at which the voltage at the first node falls.

15. The device of claim 14, wherein the voltage at the first node to falls due to operation of the one or more load circuits drawing power from the first node while the switching circuitry is opened.

16. The device of claim 14, wherein the control circuitry is configured to measure the amount that the voltage at the first node falls, or the rate at which the voltage at the first node falls, by subtracting the measured voltage from the power supply voltage.

17. The device of claim 1, further comprising a capacitance (C) in parallel with the at least one load circuit, wherein control circuitry is configured to open the switching circuitry for a time period (T), wherein the control circuitry is further configured to measure an amount the voltage at the first node falls during the time period ($\Delta V'$), and wherein the control circuitry is configured to infer the load current by calculating $C*(\Delta V'/T)$.

18. The device of claim 1, further comprising a plurality of electrodes and one or more Digital-to-Analog converters, wherein the control circuitry is configured to control the one or more Digital-to-Analog converters to provide a current to a patient's tissue.

19. The device of claim 18, wherein one of the one or more load circuits comprises a DC-DC converter that draws power from the first node, wherein the DC-DC converter is configured to produce another power supply voltage for the one or more Digital-to-Analog converters.

20. The device of claim 1, wherein the one or more load circuits comprises the control circuitry.

* * * * *